· US009220460B2

(12) United States Patent
Addison et al.

(10) Patent No.: US 9,220,460 B2
(45) Date of Patent: Dec. 29, 2015

(54) METHOD OF ANALYZING AND PROCESSING SIGNALS

(75) Inventors: Paul Stanley Addison, Edinburgh (GB); James Nicholas Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 462 days.

(21) Appl. No.: 13/590,111

(22) Filed: Aug. 20, 2012

(65) Prior Publication Data
US 2013/0046185 A1 Feb. 21, 2013

Related U.S. Application Data

(63) Continuation of application No. 10/547,430, filed as application No. PCT/GB2004/000808 on Feb. 27, 2004, now Pat. No. 8,255,029.

(30) Foreign Application Priority Data

| Feb. 27, 2003 | (GB) | 0304413.8 |
| Mar. 7, 2003 | (GB) | 0305168.7 |
| Feb. 12, 2004 | (GB) | 0403066.4 |

(51) Int. Cl.
*A61B 5/02* (2006.01)
*A61B 5/00* (2006.01)
(Continued)

(52) U.S. Cl.
CPC ............ *A61B 5/6829* (2013.01); *A61B 5/0002* (2013.01); *A61B 5/02416* (2013.01);
(Continued)

(58) Field of Classification Search
CPC . A61B 5/024; A61B 5/02416; A61B 5/02438
USPC ......... 600/323, 309, 310, 324, 481, 502, 529, 600/534
See application file for complete search history.

(56) References Cited

U.S. PATENT DOCUMENTS

| 3,532,087 A | 10/1970 | Horn |
| 3,884,219 A | 5/1975 | Richardson et al. |

(Continued)

FOREIGN PATENT DOCUMENTS

| JP | 09-084776 | 3/1997 |
| WO | WO 00-21438 | 4/2000 |

(Continued)

OTHER PUBLICATIONS

Yamada, Michio, "Wavelet Analysis and its Application," Journal of the Institute of Electronics, Information and Communication Engineers, vol. 76, No. 5, May 1993, pp. 518-528.

(Continued)

*Primary Examiner* — Michael D'Angelo
(74) *Attorney, Agent, or Firm* — Shvarts & Leiz LLP

(57) ABSTRACT

A physiological measurement system is disclosed which can take a pulse oximetry signal such as a photoplethysmogram from a patient and then analyse the signal to measure physiological parameters including respiration, pulse, oxygen saturation and movement. The system comprises a pulse oximeter which includes a light emitting device and a photodetector attachable to a subject to obtain a pulse oximetry signal; analogue to digital converter means arranged to convert said pulse oximetry signal into a digital pulse oximetry signal; signal processing means suitable to receive said digital pulse oximetry signal and arranged to decompose that signal by wavelet transform means; feature extraction means arranged to derive physiological information from the decomposed signal; an analyser component arranged to collect information from the feature extraction means; and data output means arranged in communication with the analyser component.

18 Claims, 34 Drawing Sheets

(a)

(b)

Figure 2:
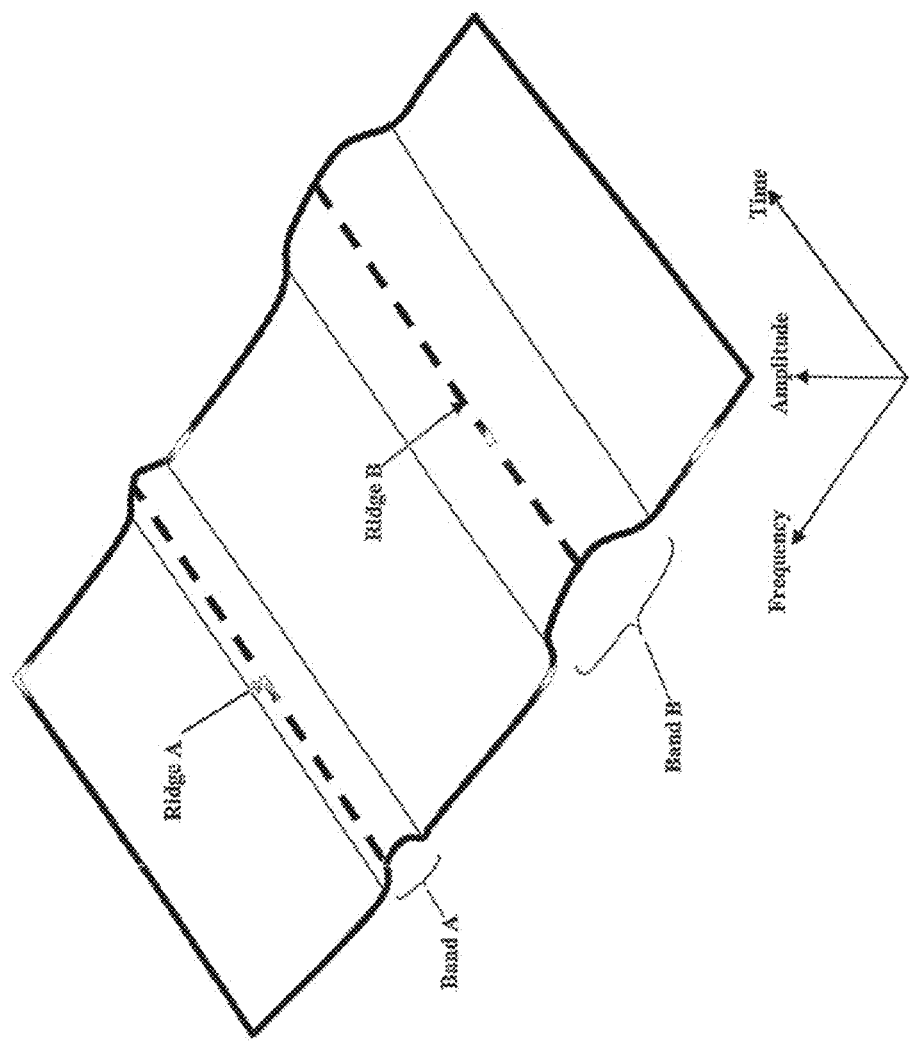

(51) Int. Cl.
    *A61B 5/024* (2006.01)
    *A61B 5/08* (2006.01)
    *A61B 5/1455* (2006.01)
    *G01N 21/31* (2006.01)

(52) U.S. Cl.
    CPC ........... *A61B5/0816* (2013.01); *A61B 5/14551* (2013.01); *A61B 5/4818* (2013.01); *A61B 5/6826* (2013.01); *A61B 5/6838* (2013.01); *A61B 5/6896* (2013.01); *A61B 5/7214* (2013.01); *A61B 5/7278* (2013.01); *G01N 21/3151* (2013.01); *A61B 5/02438* (2013.01); *A61B 2503/06* (2013.01)

(56) References Cited

U.S. PATENT DOCUMENTS

| | | |
|---|---|---|
| 3,926,177 A | 12/1975 | Hardway et al. |
| 4,289,141 A | 9/1981 | Cormier |
| 4,696,307 A | 9/1987 | Montgieux |
| 5,143,078 A | 9/1992 | Mather |
| 5,273,036 A | 12/1993 | Kronberg |
| 5,439,483 A | 8/1995 | Duong-Van |
| 5,490,505 A | 2/1996 | Diab et al. |
| 5,575,284 A | 11/1996 | Athan |
| 5,588,427 A | 12/1996 | Tien |
| 5,590,650 A | 1/1997 | Genova |
| 5,632,272 A | 5/1997 | Diab et al. |
| 5,680,871 A | 10/1997 | Ganshorn |
| 5,682,898 A | 11/1997 | Aung |
| 5,685,299 A | 11/1997 | Diab et al. |
| 5,769,785 A | 6/1998 | Diab et al. |
| 5,778,881 A | 7/1998 | Sun et al. |
| 5,795,304 A | 8/1998 | Sun et al. |
| 5,797,840 A | 8/1998 | Akselrod |
| 5,827,195 A | 10/1998 | Lander |
| 5,842,036 A | 11/1998 | Hinton et al. |
| 5,924,980 A | 7/1999 | Coetzee |
| 5,967,995 A | 10/1999 | Shusterman et al. |
| 6,002,952 A * | 12/1999 | Diab et al. .................. 600/310 |
| 6,036,642 A | 3/2000 | Diab et al. |
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,122,535 A | 9/2000 | Kaestle et al. |
| 6,129,675 A | 10/2000 | Jay |
| 6,135,952 A | 10/2000 | Coetzee |
| 6,135,966 A | 10/2000 | Ko |
| 6,142,953 A | 11/2000 | Burton |
| 6,171,257 B1 | 1/2001 | Weil et al. |
| 6,171,258 B1 | 1/2001 | Karakasoglu et al. |
| 6,206,830 B1 | 3/2001 | Diab et al. |
| 6,208,951 B1 | 3/2001 | Kumar et al. |
| 6,263,222 B1 | 7/2001 | Diab et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,398,727 B1 | 6/2002 | Bui et al. |
| 6,501,975 B2 | 12/2002 | Diab et al. |
| 6,561,986 B2 | 5/2003 | Baura |
| 6,608,934 B2 | 8/2003 | Scheirer et al. |
| 6,654,623 B1 | 11/2003 | Kastle |
| 6,702,752 B2 | 3/2004 | Dekker |
| 6,709,402 B2 | 3/2004 | Dekker |
| RE38,492 E | 4/2004 | Diab et al. |
| 6,801,798 B2 | 10/2004 | Geddes et al. |
| 6,810,277 B2 | 10/2004 | Edgar, Jr. et al. |
| 6,811,538 B2 | 11/2004 | Westbrook et al. |
| 6,896,661 B2 | 5/2005 | Dekker |
| 6,918,878 B2 | 7/2005 | Brodnick |
| 6,930,608 B2 | 8/2005 | Grajales et al. |
| 6,931,269 B2 | 8/2005 | Terry |
| 6,990,426 B2 | 1/2006 | Yoon et al. |
| 7,001,337 B2 | 2/2006 | Dekker |
| 7,020,507 B2 | 3/2006 | Scharf et al. |
| 7,035,679 B2 | 4/2006 | Addison et al. |
| 7,043,293 B1 | 5/2006 | Baura |
| 7,052,469 B2 | 5/2006 | Minamiura et al. |
| 7,054,453 B2 | 5/2006 | Causevic et al. |
| 7,054,454 B2 | 5/2006 | Causevic et al. |
| 7,079,888 B2 | 7/2006 | Oung et al. |
| 7,167,746 B2 | 1/2007 | Pederson |
| 7,171,251 B2 | 1/2007 | Sarussi |
| 7,171,269 B1 | 1/2007 | Addison et al. |
| 7,173,525 B2 | 2/2007 | Albert |
| 7,203,267 B2 | 4/2007 | De Man et al. |
| 7,225,013 B2 | 5/2007 | Geva et al. |
| 7,246,618 B2 | 7/2007 | Habashi |
| 7,254,500 B2 | 8/2007 | Makeig et al. |
| 7,289,835 B2 | 10/2007 | Mansfield et al. |
| 7,344,497 B2 | 3/2008 | Kline |
| 7,381,185 B2 | 6/2008 | Zhirnov et al. |
| 7,398,115 B2 | 7/2008 | Lynn |
| 7,421,296 B1 | 9/2008 | Benser |
| 7,515,949 B2 | 4/2009 | Norris |
| 7,519,488 B2 | 4/2009 | Fu et al. |
| 7,523,011 B2 | 4/2009 | Akiyama et al. |
| 2002/0103423 A1 | 8/2002 | Chin et al. |
| 2003/0163057 A1 | 8/2003 | Flick et al. |
| 2005/0022606 A1 | 2/2005 | Partin et al. |
| 2005/0043616 A1 | 2/2005 | Chinchoy |
| 2005/0043763 A1 | 2/2005 | Marcovecchio et al. |
| 2005/0109340 A1 | 5/2005 | Tehrani |
| 2005/0215915 A1 | 9/2005 | Noda et al. |
| 2005/0222502 A1 | 10/2005 | Cooper |
| 2005/0251056 A1 | 11/2005 | Gribkov et al. |
| 2006/0074333 A1 | 4/2006 | Huiku |
| 2006/0155206 A1 | 7/2006 | Lynn |
| 2006/0209631 A1 | 9/2006 | Melese et al. |
| 2006/0211930 A1 | 9/2006 | Scharf et al. |
| 2006/0217603 A1 | 9/2006 | Nagai et al. |
| 2006/0229519 A1 | 10/2006 | Fujiwara et al. |
| 2006/0241506 A1 | 10/2006 | Melker et al. |
| 2006/0258921 A1 | 11/2006 | Addison et al. |
| 2006/0265022 A1 | 11/2006 | John et al. |
| 2006/0282001 A1 | 12/2006 | Noel et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0129647 A1 | 6/2007 | Lynn |
| 2007/0149883 A1 | 6/2007 | Yesha |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0060138 A1 | 3/2008 | Price et al. |
| 2008/0076992 A1 | 3/2008 | Hete et al. |
| 2008/0082018 A1 | 4/2008 | Sackner et al. |
| 2008/0171946 A1 | 7/2008 | Hansmann |
| 2008/0190430 A1 | 8/2008 | Melker et al. |
| 2008/0202525 A1 | 8/2008 | Mitton et al. |
| 2008/0214903 A1 | 9/2008 | Orbach |
| 2008/0243021 A1 | 10/2008 | Causevic et al. |
| 2009/0324034 A1 | 12/2009 | Watson et al. |
| 2009/0326871 A1 | 12/2009 | Watson et al. |
| 2010/0014761 A1 | 1/2010 | Addison et al. |
| 2011/0004069 A1 | 1/2011 | Ochs et al. |

FOREIGN PATENT DOCUMENTS

| | | |
|---|---|---|
| WO | WO 01-25802 | 4/2001 |
| WO | WO 01-62152 | 8/2001 |
| WO | WO 01-76471 | 10/2001 |
| WO | WO 01-82099 | 11/2001 |
| WO | WO 03-00125 | 1/2003 |
| WO | WO 03-55395 | 7/2003 |
| WO | WO 2004-075746 | 9/2004 |
| WO | WO 2004-105601 | 12/2004 |

(56) References Cited

FOREIGN PATENT DOCUMENTS

| WO | WO 2005-096170 | 10/2005 |
|---|---|---|
| WO | WO 2006-085120 | 8/2006 |
| WO | WO 2008-043864 | 8/2008 |

OTHER PUBLICATIONS

Addison, Paul S., The Illustrated Wavelet Transform Handbook, Taylor & Francis Group, 2002.

Addison, P. et al., "Secondary Wavelet Feature Decoupling (SWFD) and its use in Detecting Patient Respiration from the Photoplethysmogram", Proceedings of the 25th Annual International Conference of the IEEE Engineering in Medicine and Biology Society, Cancun, Mexico, Sep. 17-21, 2003, vol. 3 of 4, pp. 2602-2605.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 20:33-36, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95:1124-1128.

Dowla, Farid U., et al. "Neural networks and wavelet analysis in the computer interpretation of pulse oximetry data." *Neural Networks for Signal Processing [1996] VI. Proceedings of the 1996 IEEE Signal Processing Society Workshop*, pp. 527-536, IEEE, 1996.

Rusch, T. L., et al. "Signal processing methods for pulse oximetry." *Computers in biology and medicine* 26.2 (1996), pp. 143-159.

Kim, J. M., et al. "Signal processing using Fourier & wavelet transform for pulse oximery." *Lasers and Electro-Optics, 2001. CLEO/Pacific Rim 2001. The 4th Pacific Rim Conference on Lasers and Electro-Optics*, vol. 2, pp. 310-311, IEEE, 2001.

Leonard, P., et al. "Standard pulse oximeters can be used to monitor respiratory rate." *Emergency medicine journal* 20.6 (2003), pp. 524-525.

Addison, Paul S., et al. "Rapid Communication: A novel time-frequency-based 3D Lissajous figure method and its application to the determination of oxygen saturation from the photoplethysmogram." *Measurement Science and Technology* 15 (2004), pp. L15-L18.

Addison, Paul S., et al. "Oxygen saturation determined using a novel wavelet ratio surface." *Medical engineering & physics* 27.3 (2005), pp. 245-248.

\* cited by examiner

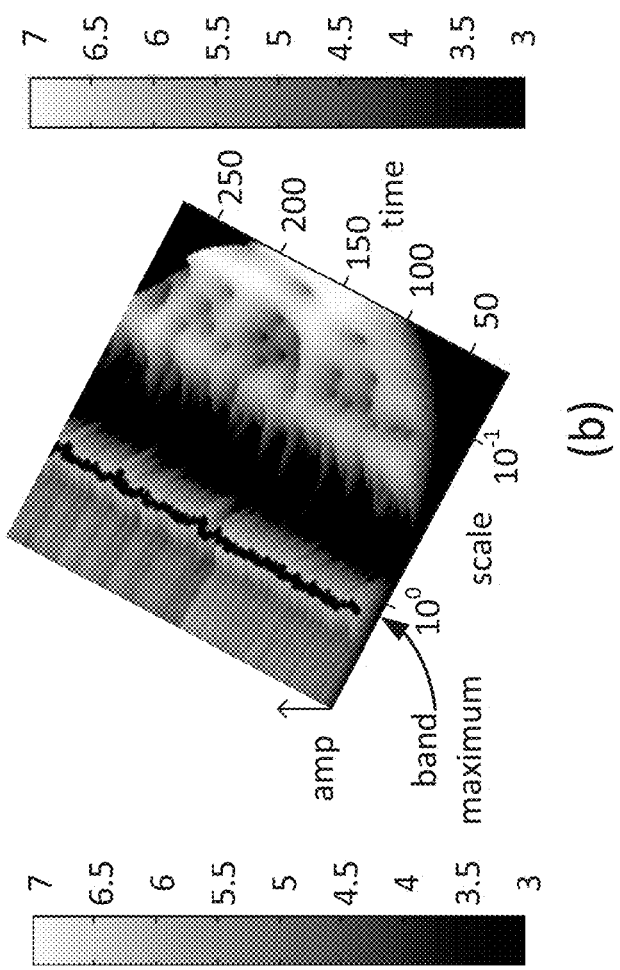
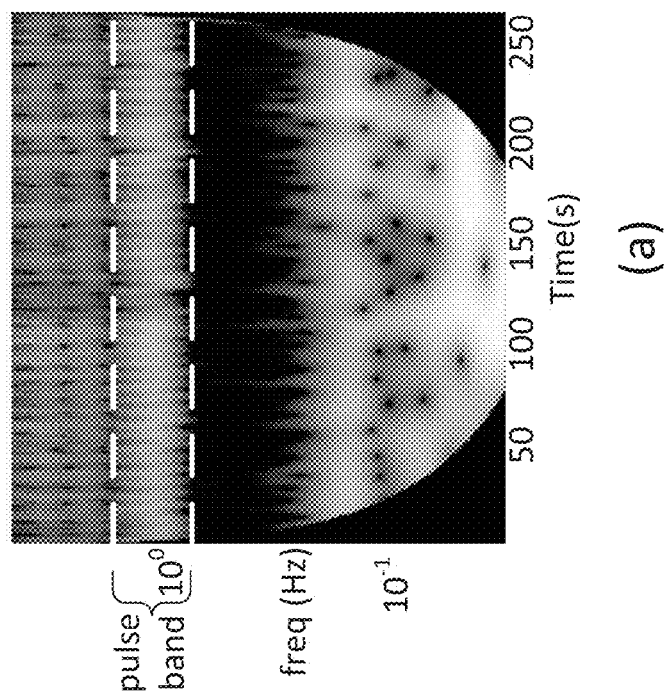
Figure 1

(b)

METHOD OF ANALYZING AND PROCESSING SIGNALS

CROSS REFERENCE TO RELATED APPLICATIONS

This is a continuation of U.S. patent application Ser. No. 10/547,430, filed Dec. 1, 2005, which is the United States National Stage of International Patent Application No. PCT/GB2004/000808, filed Feb. 27, 2004, which designated the United States and which claims the benefit under 35 U.S.C. §119 of Foreign Priority Applications GB0304413.8, filed Feb. 27, 2003, GB0305168.7, filed Mar. 7, 2003, and GB0403066.4, filed Feb. 12, 2004, each of which is hereby incorporated herein by reference in its respective entirety.

1. INTRODUCTION

Problem Domain/Field of Invention

The present invention relates to a method of analysing and processing signals. More specifically the invention relates to the analysis and processing of photoplethysmogram (PPG) signals. The invention uses wavelet transform methods to derive clinically useful information from the PPG including information regarding the respiration, pulse, oxygen saturation, and patient movement. This information may be used within a device, to monitor the patient within a range of environments including the hospital and home environments. In one preferred embodiment the device may be used to detect irregularities in one or more of the derived signals: respiration, pulse, oxygen saturation and movement. The device allows output of this information in a clinically useful form and incorporates an alarm which is triggered when one or a combination of signal irregularities are detected. Of particular note is that the utility of current pulse oximeter devices is greatly increased through the provision of a robust measure of patient respiration directly from the PPG signal.

2. BACKGROUND

2.1 Blood Oxygen Saturation and its Measurement

Oximetry is an optical method for measuring oxygen saturation in blood. Oximetry is based on the ability of different forms of haemoglobin to absorb light of different wavelengths. Oxygenated haemoglobin ($HbO_2$) absorbs light in the red spectrum and deoxygenated or reduced haemoglobin (RHb) absorbs, light in the near-infrared spectrum. When red and infrared light is passed through a blood vessel the transmission of each wavelength is inversely proportional to the concentration of $HbO_2$ and RHb in the blood. Pulse oximeters can differentiate the alternating light input from arterial pulsing from the constant level contribution of the veins and other non-pulsatile elements. Only the alternating light input is selected for analysis. Pulse oximetry has been shown to be a highly accurate technique. Modern pulse oximeter devices aim to measure the actual oxygen saturation of the blood ($SaO_2$) by interrogating the red and infrared PPG signals. This measurement is denoted $SpO_2$. The aim of modern device manufacturers is to achieve the best correlation between the pulse oximeter measurement given by the device and the actual blood oxygen saturation of the patient. It is known to those skilled in the art that in current devices a ratio derived from the photoplethysmogram (PPG) signals acquired at the patients booty is used to determine the oxygen saturation measurement using a look up table containing a pluracy of corresponding ratio and saturation values. Modern pulse oximeter devices also measure patient heart rate. Current devices do not provide a measure of respiration directly from the PPG signal. Additional expensive and obtrusive equipment is necessary to obtain this measurement.

2.2 Time-Frequency Analysis in Wavelet Space

The wavelet transform of a signal x(t) is defined as $$T(a, b) = \frac{1}{\sqrt{a}} \int_{-\infty}^{+\infty} x(t) \psi^*\left(\frac{t-b}{a}\right) dt \quad [1]$$

where $\psi^*(t)$ is the complex conjugate of the wavelet function $\psi(t)$, a is the dilation parameter of the wavelet and b is the location parameter of the wavelet. The transform given by equation (1) can be used to construct a representation of a signal on a transform surface. The transform may be regarded as a time-scale representation or a time-frequency representation where the characteristic frequency associated with the wavelet is inversely proportional to the scale a. In the following discussion 'time-scale' and 'time frequency' may be interchanged. The underlying mathematical detail required for the implementation within a time-scale or time-frequency framework can be found in the general literature, e.g. the text by Addison (2002).

The energy density function of the wavelet transform, the scalogram, is defined as $$S(a,b) = |T(a,b)|^2 \quad [2]$$

where '| |' is the modulus operator. The scalogram may be resealed for useful purpose. One common repealing is defined as $$S_R(a, b) = \frac{|T(a, b)|^2}{a} \quad [3]$$

and is useful for defining ridges in wavelet space when, for example, the Morlet wavelet is used. Ridges are defined as the locus of points of local maxima in the plane. Any reasonable definition of a ridge may be employed in the method. We also include as a definition of a ridge herein paths displaced from the locus of the local maxima. A ridge associated with only the locus of points of local maxima in the plane we label a 'maxima ridge'. For practical implementation requiring fast numerical computation the wavelet transform may be expressed in Fourier space and the Fast Fourier Transform (FFT) algorithm employed. However, for a real time application the temporal domain convolution expressed by equation (1) may be more appropriate. In the discussion of the technology which follows herein the 'scalogram' may be taken to the include all reasonable forms of repealing including but not limited to the original unsealed wavelet representation, linear rescaling and any power of the modulus of the wavelet trans forts may be used in the definition.

As described above the time-scale representation of equation (1) may be converted to a time-frequency representation. To achieve this, we must convert from the wavelet a scale (which can be interpreted as a representative temporal period) to a characteristic frequency of the wavelet function. The characteristic frequency associated with a wavelet of arbitrary a scale is given by $$f = \frac{f_c}{a} \quad [4]$$

where $f_c$, the characteristic frequency of the mother wavelet (i.e. at a=1), becomes a scaling constant and f is the representative or characteristic frequency for the wavelet at arbitrary scale a.

Any suitable wavelet function may be used in the method described herein. One of the most commonly used complex wavelets, the Morlet wavelet, is defined as;

$$\psi(t) = \pi^{-1/4}(e^{i2\pi f_0 s} - e^{-(2\pi f_0)^2/2})e^{-t^2/2} \quad [5]$$

where $f_0$ is the central frequency of the mother wavelet. The second term in the brackets is known as the correction term, as it corrects for the non-zero mean of the complex sinusoid within the Gaussian window. In practice it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad [6]$$

This wavelet is simply a complex wave within a Gaussian envelope. We include both definitions of the Morlet wavelet in our discussion here. However, note that the function of equation (6) is not strictly a wavelet as it has a non-zero mean, i.e. the zero frequency term of its corresponding energy spectrum is non-zero and hence it is inadmissible. However, it will be recognised by those skilled in the art that it can be used in practice with $f_0 \gg 0$ with minimal error and we include it and other similar near wavelet functions in our definition of a wavelet herein. A more detailed overview of the underlying wavelet theory, including the definition of a wavelet function, can be found in the general literature, e.g. the text by Addison (2002). Herein we show how wavelet transform features may be extracted from the wavelet decomposition of pulse oximeter signals and used to provide a range of clinically useful information within a medical device.

3. WAVELET FEATURE EXTRACTION

In this section, methods are described for the extraction and use of wavelet features from the PPG signals for use in the provision of clinically useful information. These are incorporated within a medical device and the information is output in a range of formats for use in the monitoring of the patient. The device comprises four key components for the utilisation of the wavelet transform information, these are the Pulse Component, Respiration Monitoring Component, Oxygen Saturation Component and the Movement Component. The underlying theory pertaining to these components is detailed below.

3.1 Pulse Component

Pertinent repeating features in the signal gives rise to a time-frequency band in wavelet space or a resealed wavelet space. For example the pulse component of a photoplethysmogram (PPG) signal produces a dominant band in wavelet space at or around the pulse frequency. FIGS. 1(a) and (b) contains two views of a scalogram derived from a PPG signal. The figures show an example of the band caused by the pulse component in such a signal. The pulse band is located between the dashed lines in the plot of FIG. 1(a) The band is formed from a series of dominant coalescing features across the scalogram. This can be clearly seen as a raised band across the transform surface in FIG. 1(b) located within a region at just over 1 Hz, i.e. 60 breaths per minute. The maxima of this band with respect to frequency is the ridge. The locus of the ridge is shown as a black curve on top of the band in FIG. 1(b). By employing a suitable rescaling of the scalogram, such as that given in equation 3, we can relate the ridges found in wavelet space to the instantaneous frequency of the signal. In this way the pulse frequency (pulse rate) may be obtained, from the PPG signal. Instead of repealing the scalogram, a suitable predefined relationship between the frequency obtained from the ridge on the wavelet surface and the actual pulse frequency may also be used to determine the pulse rate.

By mapping the time-frequency coordinates of the pulse ridge onto the wavelet phase information gained through the wavelet transform, individual pulses may be captured. In this way both times between individual pulses and the timing of components within each pulse can be monitored and used to detect heart beat anomalies, measure arterial system compliance, etc. Alternative definitions of a ridge may be employed. Alternative relationships between the ridge and the pulse frequency may be employed.

3.2 Respiration Monitoring Component

The respiration monitoring component uses wavelet based methods for the monitoring of patient respiration. This can include the measurement of breathing rate and the identification of abnormal breathing patterns including the cessation of breathing. A key part of the respiration monitoring component is the use of secondary wavelet feature decoupling (SWFD) described below. The information concerning respiration gained from the application of SWFD can then be compared and/or combined with respiration information from other methods to provide a respiration measure output.

As stated above, pertinent repeating features in the signal give rise to a time-frequency band in wavelet space or a rescaled wavelet space. For a periodic signal this band remains at a constant frequency level in the time frequency plane. For many real signals, especially biological signals, the band may be non-stationary) varying in characteristic frequency and/or amplitude over time. FIG. 2 shows a schematic of a wavelet transform of a signal containing two pertinent components leading to two bands in the transform apace. These bands are labeled band A and band B on the three-dimensional (3-D) schematic of the wavelet surface. We define the band ridge as the locus of the peak values of these bands with respect to frequency. For the purposes of the discussion of the method we assume that band B contains the signal information of interest. We will call this the 'primary band'. In addition, we assume that the system from which the signal originates, and from which the transform is subsequently derived, exhibits some form of coupling between the signal components in band A and band B.

Figure 3:
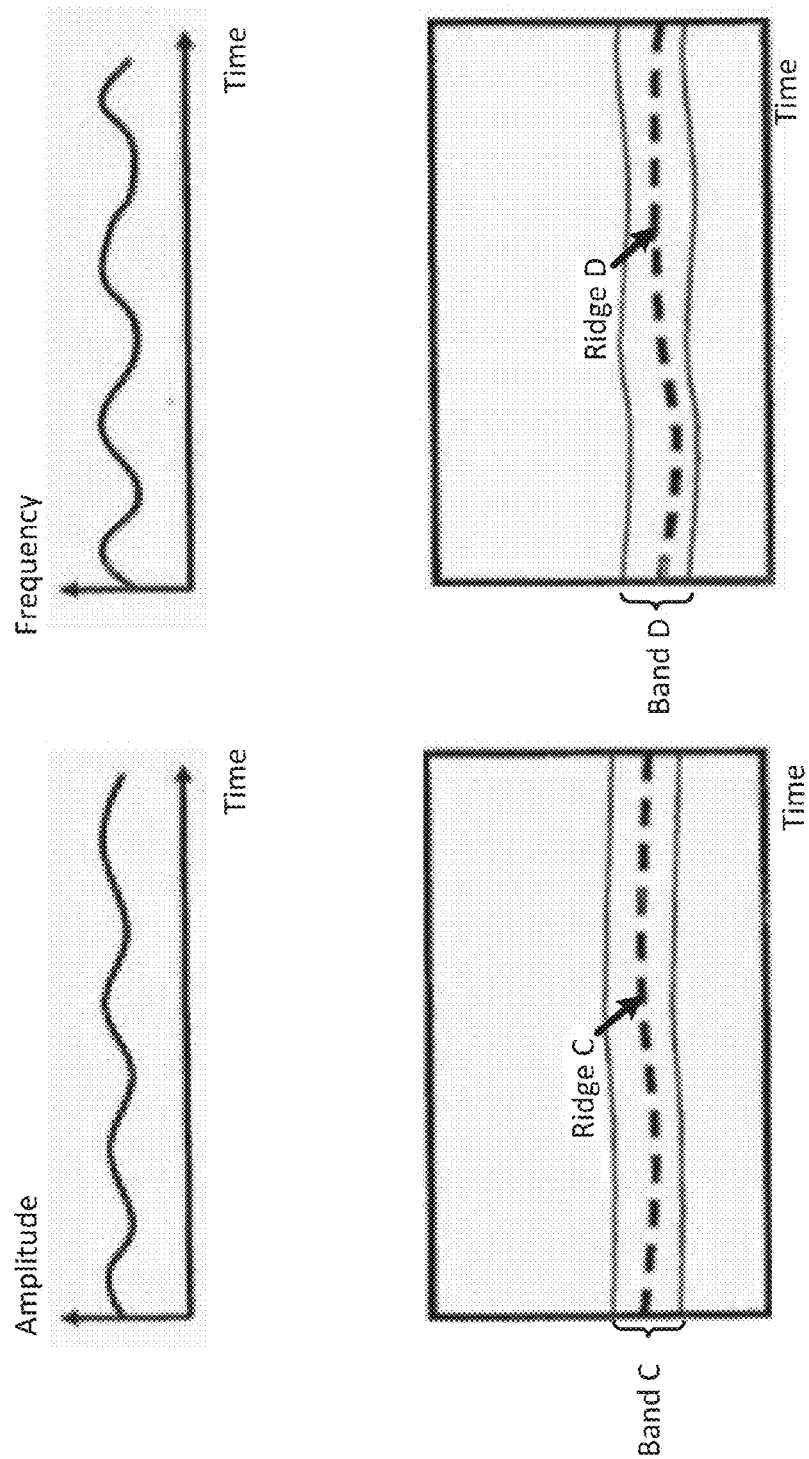

When noise or other erroneous features are present in the signal with similar spectral characteristics of the features of band B then the information within band B can become ambiguous, i.e. obscured, fragmented or missing. In this cane the ridge of band A can be followed in wavelet space and extracted either as an amplitude signal or a frequency signal which we call the 'ridge amplitude perturbation (RAP) signal' and the 'ridge frequency perturbation (RFP) signal' respectively. The RAP and RFP signals are extracted by projecting the ridge onto the time-amplitude or time-frequency planes respectively. The top plots of FIG. 3 shows a schematic of the RAP and RFP signals associated with ridge A in FIG. 2. Below these RAP and RFP signals we can see schematics of a further wavelet decomposition of these newly derived signals. This secondary wavelet decomposition allows for information in the spectral region of band B in FIG. 2 to be made available as band C and band D. The ridges of bands C and D can serve as instantaneous time-frequency characteristic measures of the signal components causing bands C and D. This method, which we call Secondary Wavelet Feature Decoupling (SWFD), therefore allows information concerning the nature of the signal components associated with the underlying physical process causing the primary band B (FIG. 2) to be extracted when band B itself is obscured in the presence of noise or other erroneous signal features.

Figure 4:
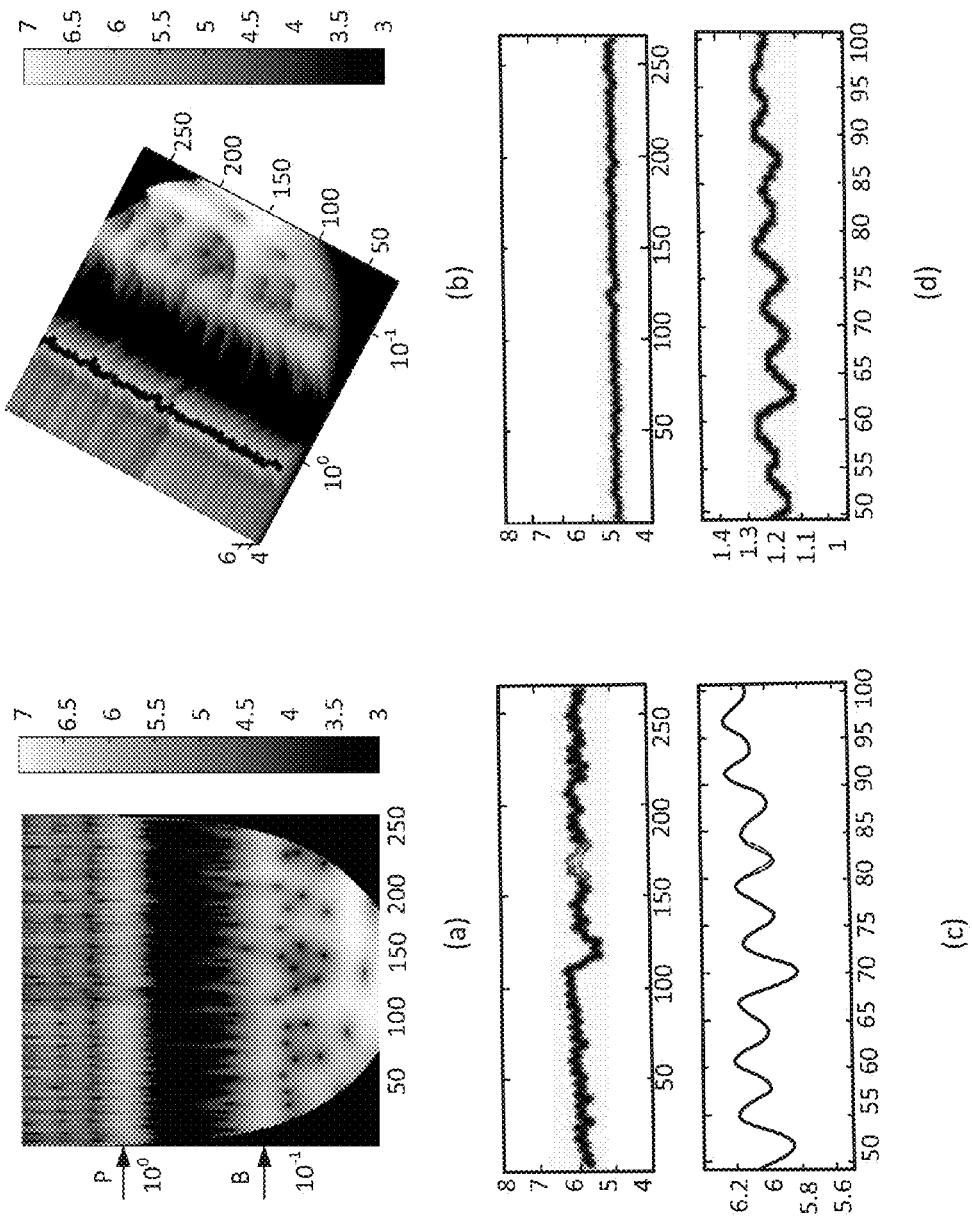
Figure 5:
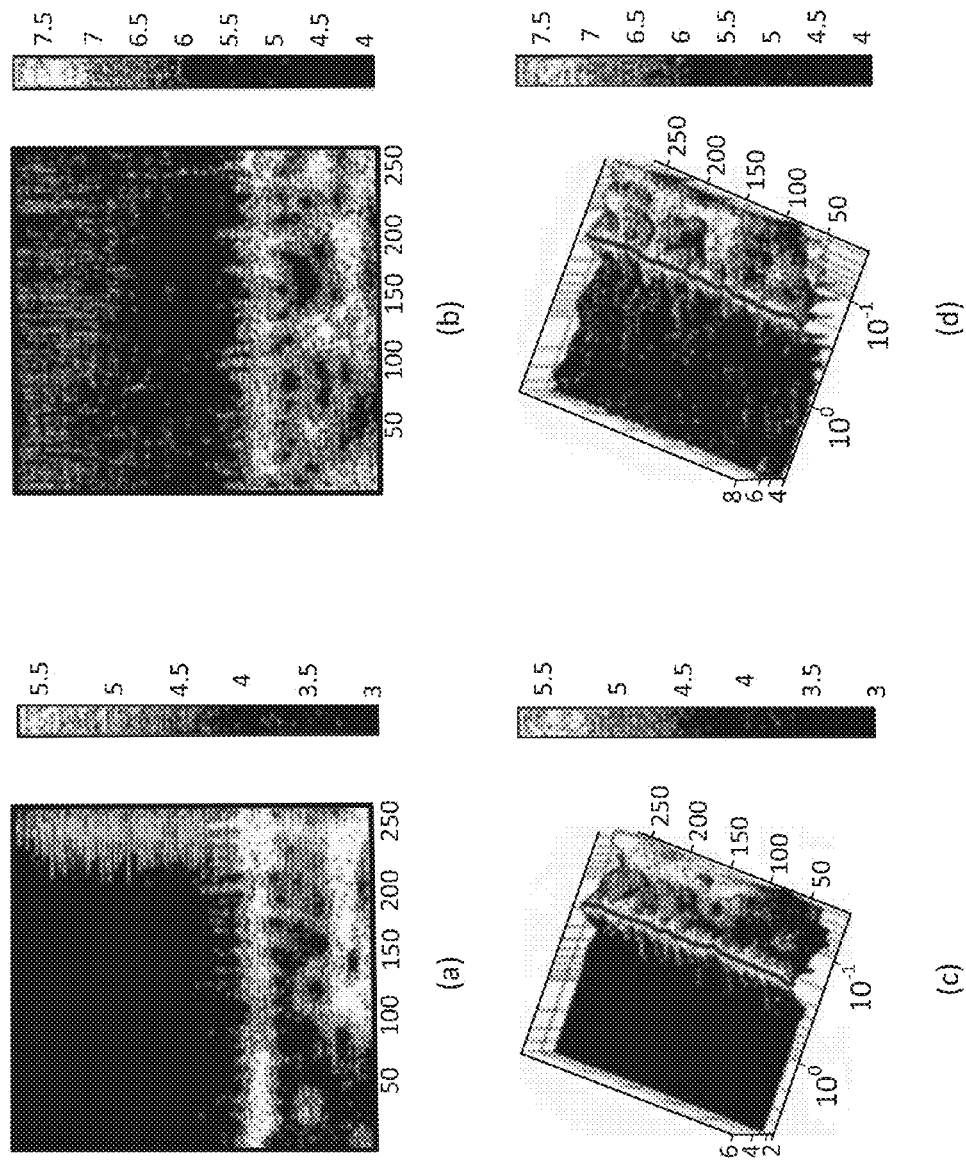
Figure 6:
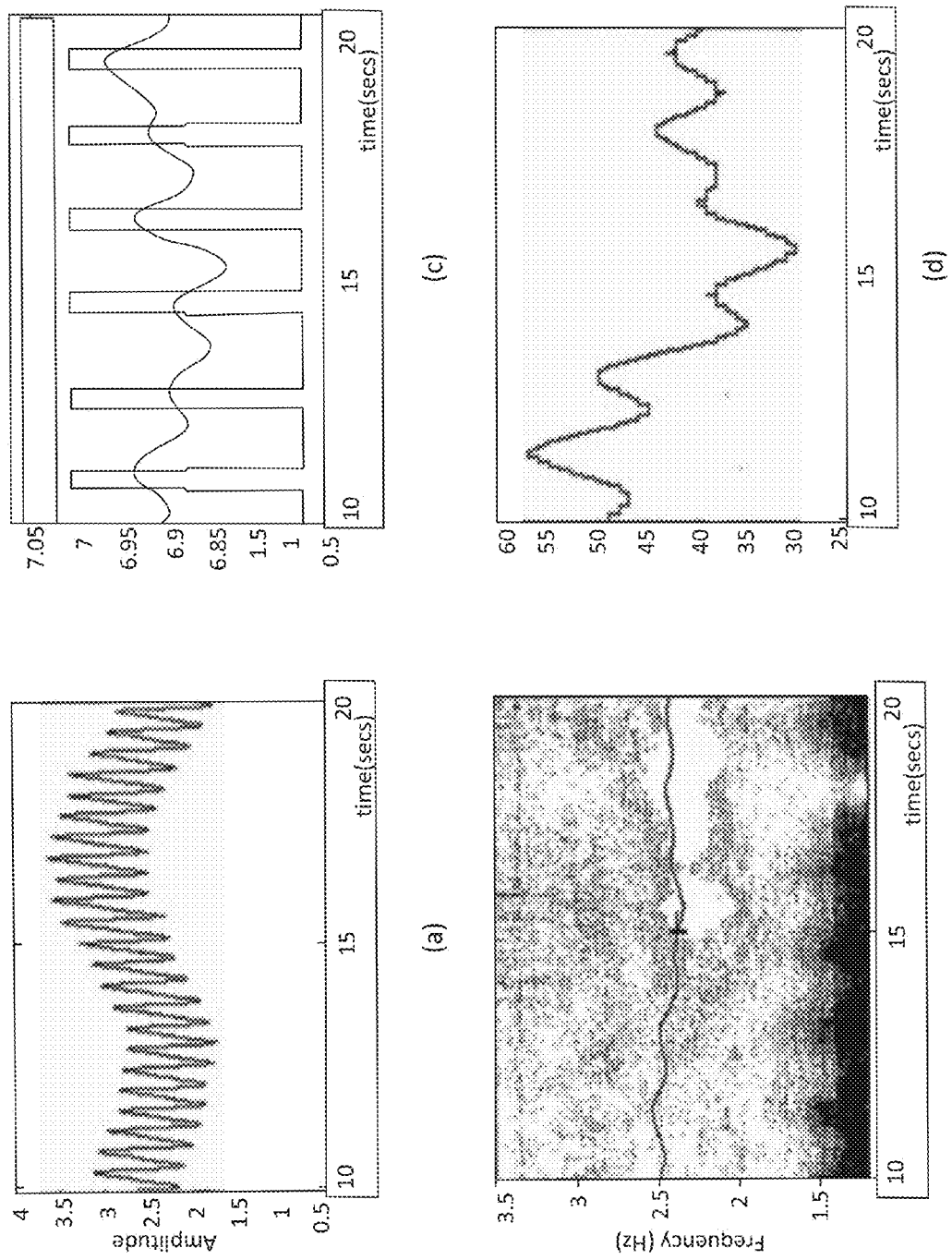
Figure 7:
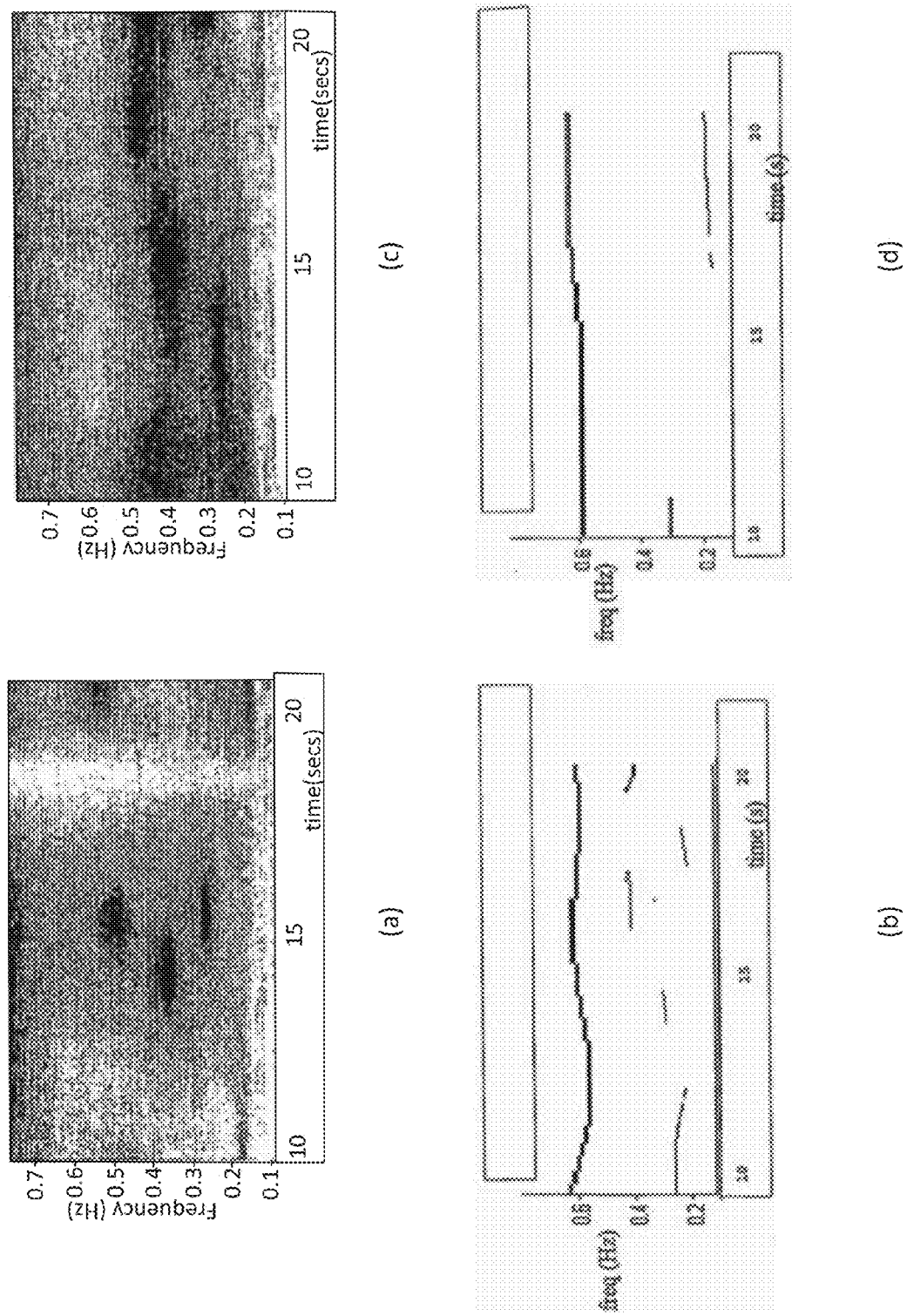
Figure 8:
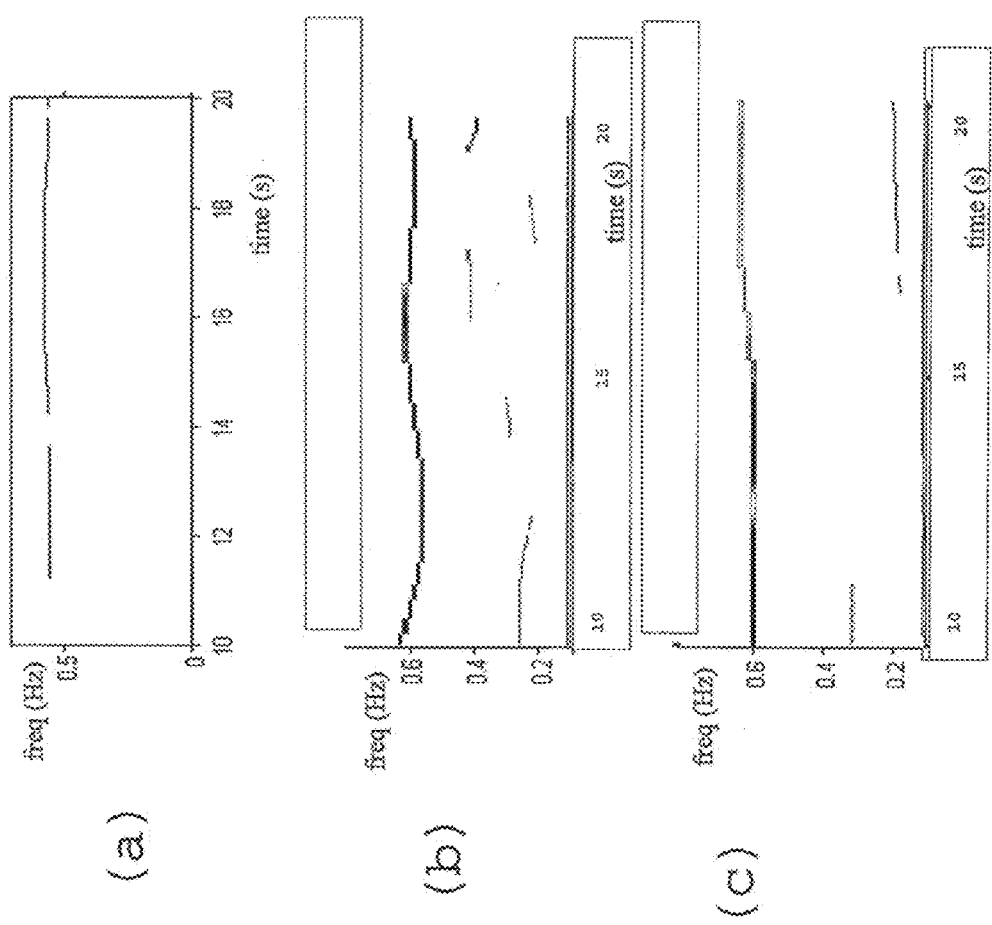
Figure 8:
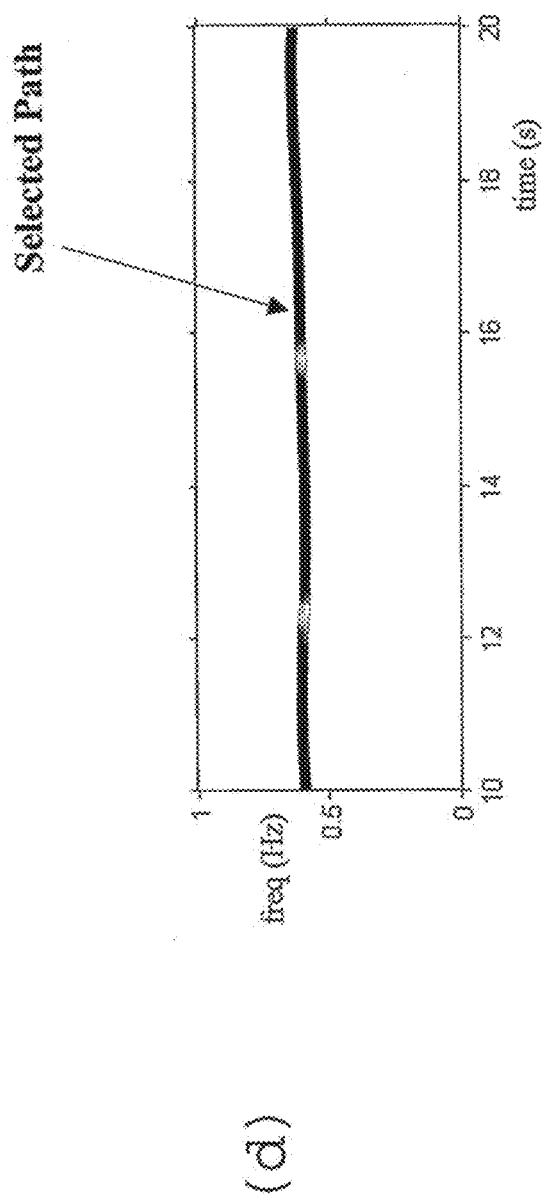

An example of the SWFD method used on a PPG signal to detect patient breathing from the ridge associated with patient pulse is shown in FIGS. 4 and 5. Daring the experiment from which the signal was taken the patient was breathing regularly at breaths of 6 seconds duration (=0.167 Hz).

FIG. 4(a) contains the scalogram derived from the PPG trace taken during the experiment. Two dominant bands appear in the plots the pulse band and a band associated with patient breathing. These are marked P and B respectively in the plot. In this example we are concerned with the detection of breathing through time and hence here the breathing band is the primary band. The pulse band appears at just over 1 Hz, or 60 beats per minute, the beat frequency of the heart and the breathing band appears at 0.167 Hz corresponding to the respiration rate. However, the identification of breathing features is often masked by other low frequency artefact in these signals. One such low frequency artefact feature, 'F', is indicated in the plot within the dotted ellipse marked on the scalogram where it can be seen to interfere with the breathing band. FIG. 4(b) contains a 3-D view of the scalogram plot shown in FIG. 4(a). From the 3-D plot we can see that the low frequency artefact feature causes a bifurcation of the breathing band at the location, shown by the arrow in the plot. The pulse ridge is also shown on FIG. 4(b), indicated by the black curve along the pulse band. This is the locus of the maxima with respect to frequency along the pulse band.

FIG. 4(c) contains the RAP signal derived from, the pulse ridge shown in FIG. 4(b) where the pulse ridge is followed and its amplitude is plotted against time. The top plot of FIG. 4(c) contains the whole RAP signal. The lower plot of FIG. 4(c) contains a blow up of the RAP signal over a 50 seconds interval. An obvious modulation with a period of 6 seconds can be seen in this blow up. The top plot of FIG. 4(d) contains the whole RFP signal corresponding to the pulse ridge in FIG. 4(b). The lower plot of FIG. 4(d) contains a blow up of the RFP signal over 50 seconds. Again an obvious modulation (of 6 second period) can be seen in this blow up.

A second wavelet transform was then performed on the RAP and RFP signals. The resulting scalograms corresponding to the RAP and RFP signals are shown in FIGS. 5a and 5b respectively and the 3-D plots of these scalograms are shown in FIGS. 5c and 5d respectively. The breathing ridges derived from the RAP and RFP scalograms are superimposed on the 3-D scalograms. The RAP scalogram is the cleaner of the two and can be seen not to contain interference from the artefact feature 'F' found in the original signal scalogram of FIG. 4(a). For this example the RAP scalogram provides the best solution for the removal of erroneous signal features and the identification of the breathing band when compared to the original scalogram and the RFP scalogram. In practice all three scalograms are compared and the optimal scalogram or combination of scalograms for the extraction of the information required is determined.

Through experimentation covering a variety of patient groups (e.g. adult, child, neonate) we have found that for certain signals the method can be enhanced by incorporating paths displaced from the band ridge in the SWFD method. In these cases the SAP signals derived from the displaced path exhibits much larger oscillations (compared to the low frequency background waveform) than those of the original ridge path. We find that this enhancement allows us to better detect the breathing component within the SWFD method. Hence we extend our definition of a surface ridge as employed in the method to include paths displaced from the locus of the peak values, contours at a selected level of the pulse band, and in general any reasonably constructed path within the vicinity of the pertinent feature under investigation, where the vicinity is taken to be within the region, of the corresponding band.

From the above example it can be seen how a secondary wavelet transform of wavelet transform ridge information derived from the pulse band ridge may be used to provide a clearer manifestation of the breathing features in wavelet space from which pertinent breathing information may be derived.

The SWFD method described above can form the basis of completely new algorithms for incorporation within devices which require the detection of otherwise masked signal components. Herein, we show the application of the method to the detection of breathing features from within the photoplethysmogram, although it will be recognised by those skilled in the art that the method may be applied to other problematic signals.

In practice, both the original direct observation of the primary band and the indirect observation through perturbations to the secondary band may be employed simultaneously and the optimal time-frequency information extracted.

Those skilled in the art will recognise that modifications and improvements can be incorporated within the methodology outlined herein without departing from the scope of the Invention.

Those skilled in the art will recognise that the above methods may be performed using alternative time-frequency representations of the signals where the amplitude in the time-frequency transform space can be related to the amplitude of pertinent features within the signal. In addition the decomposition of the original signal and the subsequent decompositions of the RFP and RAP scalograms may be performed, each with a different time-frequency method. However, in the preferred method the continuous wavelet transform is employed in all decompositions, although different wavelet functions may be employed in each of the wavelet transforms employed in the method.

The preferred method detailed herein departs from alternate methods to probe the time-frequency information, within wavelet space which follow paths of constant frequency in wavelet space. The current method involves following a selected path in wavelet space from which new signals are derived. This allows signal components with non-stationary frequency characteristics to be followed and analysed to provide information of other signal components which may also exhibit non-stationary behaviour.

It will be obvious to those skilled in the art that the method relies on high resolution in wavelet space hence the continuous wavelet, transform is the preferred method. (The time-frequency discretisation employed by the discrete wavelet transform and the stationary wavelet transform is, in general, too coarse for the useful application of the method.) The continuous wavelet, transform is implemented in the method through a fine discretisation in both time and frequency.

Although the method herein has been described in the context of the detection of breathing features from the pulse band of the wavelet transform of the photoplethysmogram, those skilled in the art will recognise that the method has wide applicability to other signals including, but not limited to: other biosignals (e.g. the electrocardiogram, electroencephalogram, electrogastrogram, electromyogram, heart rate signals, pathological sounds, and ultrasound), dynamic signals, non-destructive testing signals, condition monitoring signals, fluid signals, geophysical signals, astronomical signals, electrical signals, financial signals including financial indices, sound, and speech signals, chemical signals, and meteorological signals including climate signals.

In summary a method for the decomposition of signals using wavelet transforms has been described which allows for underlying signal features which are otherwise masked to be detected. The method is described in the following steps (a) A wavelet transform decomposition of the signal is made.
(b) The transform surface is inspected in the vicinity of the characteristic frequency of the pertinent signal feature to detect the dominant band (the primary band) associated with the pertinent feature. This band is then interrogated to reveal information corresponding to the pertinent feature. This interrogation may include ridge following methods for identification of localised frequencies in the time-frequency plane.
(c) A secondary band is then identified outwith the region of the pertinent feature and its ridge identified.
(d) The time-frequency and time-amplitude locus of points on the secondary ridge are then extracted. These new signals are denoted the 'ridge amplitude perturbation (RAP) signal' and the 'ridge frequency perturbation (RFP) signal' respectively.
(e) A wavelet transformation of the RAP and RFP signals is then carried out to give the RAP and RFP scalograms respectively.
(f) These secondary scalograms are then interrogated to reveal information in the region of the primary band of the original scalogram. This interrogation may include ridge following methods for identification of localised frequencies in the time-frequency plane.
(g) The information gained from step (b) and step (f) are then used to provide the optimal signal information pertaining to the signal feature or features under investigation.

More than one secondary band may be present. These additional secondary bands may be interrogated in the same way, i.e. steps (c) to (g).

In the context of breathing detection from the photoplethysmogram the 'primary band' referred to in the above is the breathing band and the 'secondary band' is the pulse band. In the method one or more or a combination of PPG signals may be employed.

In an alternative methodology once the RAP and RFP signals have been abstracted, in step (d) these are then interrogated over short segments using an alternative time-frequency or frequency based method (e.g. using a standard FFT routine to find a dominant peak associated with the primary band signal) or another method of signal repetition including, but not limited to, turning points of the signal. This may be employed to speed up the computation of the characteristic frequency of the RAP and RFP scalogram bands or to enhance the technique.

In step (d) above a combination of the RAP and RFP signals may also be used to generate a representative signal for secondary wavelet decomposition.

Patient respiration information from the secondary wavelet feature decoupling incorporating the RAP and RFP signals is used directly to monitor patient respiration. This can include the measurement of breathing rate and the identification of abnormal breathing patterns including the cessation of breathing. Either the RAP-based SWFD or the RFP-based SWFD information may be chosen for patient respiration monitoring. Alternatively a combination of both may be employed where the respiration information derived from each method may be graded quantitatively according to a confidence measure.

Further the respiration information gained from the RAP-based SWFD and the RFP-based SWFD may be compared to and/or combined with respiration information gained from other methods to provide an optimal output for respiration measures including respiration rate, breath timings, breathing anomalies, etc. These other methods may include that described in International Patent Application No PCT/GB02/02843, "Wavelet-based Analysis of Pulse Oximetry signals" by Addison and Watson. The chosen respiration measure for output will be extracted using a polling mechanism based on a quantitative measure of the quality of the respiration information derived by each method.

FIGS. 6 to 10 illustrate the preferred embodiment of the respiration monitoring methodology. The wavelet transform of the PPG signal (FIG. 6(a)) is computed. A plot of the resulting scalogram is shown in FIG. 6(b). The 10 second PPG signal used in this example was taken from a premature neonate. The same methodology also works for adult and child PPGs. The pulse ridge is shown plotted as a black path across the scalogram in FIG. 6(b) at around 2.5 Hz—typical for these young patients. The RAP and RFP signals are then derived from the pulse ridge of the wavelet transform. The RAP and RFP signals are shown respectively. In FIG. 6(c) and FIG. 6(d). Also shown in FIG. 6(c) is the patient switch signal which shows inspiration and expiration of the patient as a high/low amplitude square wave trace. The switch signal was activated by an observer monitoring the movement of the chest wall of the neonate during the experiment. The turning points in the RAP and RFP signals may be used as an initial detection mechanism for individual breaths. The RFP and RAP signals are assessed for quality using a confidence measure. This measure may be based on any reasonable measure including but not limited to the entropy of the signals. The signal with the highest confidence is used to extract information on individual breaths and a breathing rate using the average duration of a number of recently detected breaths. A second wavelet transform is performed on both signals. The result of a second wavelet, transform on the RAP signal of FIG. 6(c) is shown in FIG. 7(a) and the ridges of this transform surface are extracted as shown in FIG. 7(b). The result of a second wavelet transform on the RFP signal of FIG. 6(d) is shown in FIG. 7(c) and the ridges of this transform surface are extracted as shown in FIG. 7(d).

The extracted ridges from the RFP and RAP signal transforms and the ridges found in the original transform in the region of respiration, shown in FIGS. 8(a), (b) and (c) respectively, are then analysed to determine a composite path which we call the 'selected respiration path' SRP. The analysis may include, but is not limited to, the intensities and locations of the ridges. The SRP represents the most likely breathing components. The SRP derived from the extracted ridges shown in FIGS. 8(a), (b) and (c) is shown in FIG. 8(d). The SRP will normally be determined within an initial pre-determined "latch-on" time window and reassessed within an updated time window. The ridge selection procedure used to derive the SRP is based upon a decision tree implementing a weighted branching dependent upon, tout not limited to, the following local (i.e. relationship between ridge components within a particular ridge set) and global (i.e. the inter-relationship between ridge components across ridge sets) criteria: start and end position, length, average and peak strengths, various spatial (i.e. movement range over the time-frequency surface) statistical parameters including variance and entropy, and a measurement of relative switchback positions (i.e. degree of overlap with other ridges). These criteria are based on results of our in house experimentation across a range of patient categories: adult, child and neonate.

A confidence metric for the accuracy of the SWFD ridge obtained from the RAP signal can also be acquired by comparing the resultant SWFD ridge intensities derived from the RAP signal of the band maxima ridge and ridges off-set from it. When compared to RAP-SWFD derived from the band maxima ridge, the off-ridge transform's ridges associated with respiration have been observed to increase (to a maximum) in intensity as the displacement of the off-ridge from the maxima ridge is increased. Those ridges associated with other features, however, remain relatively static in amplitudes. In this way, by interrogating the ridge amplitudes of a plurality of RAP signals derived from the band maxima offsets, the ridge or ridges associated with respiration can be identified through a significant change in amplitude relative to others.

Figure 9:
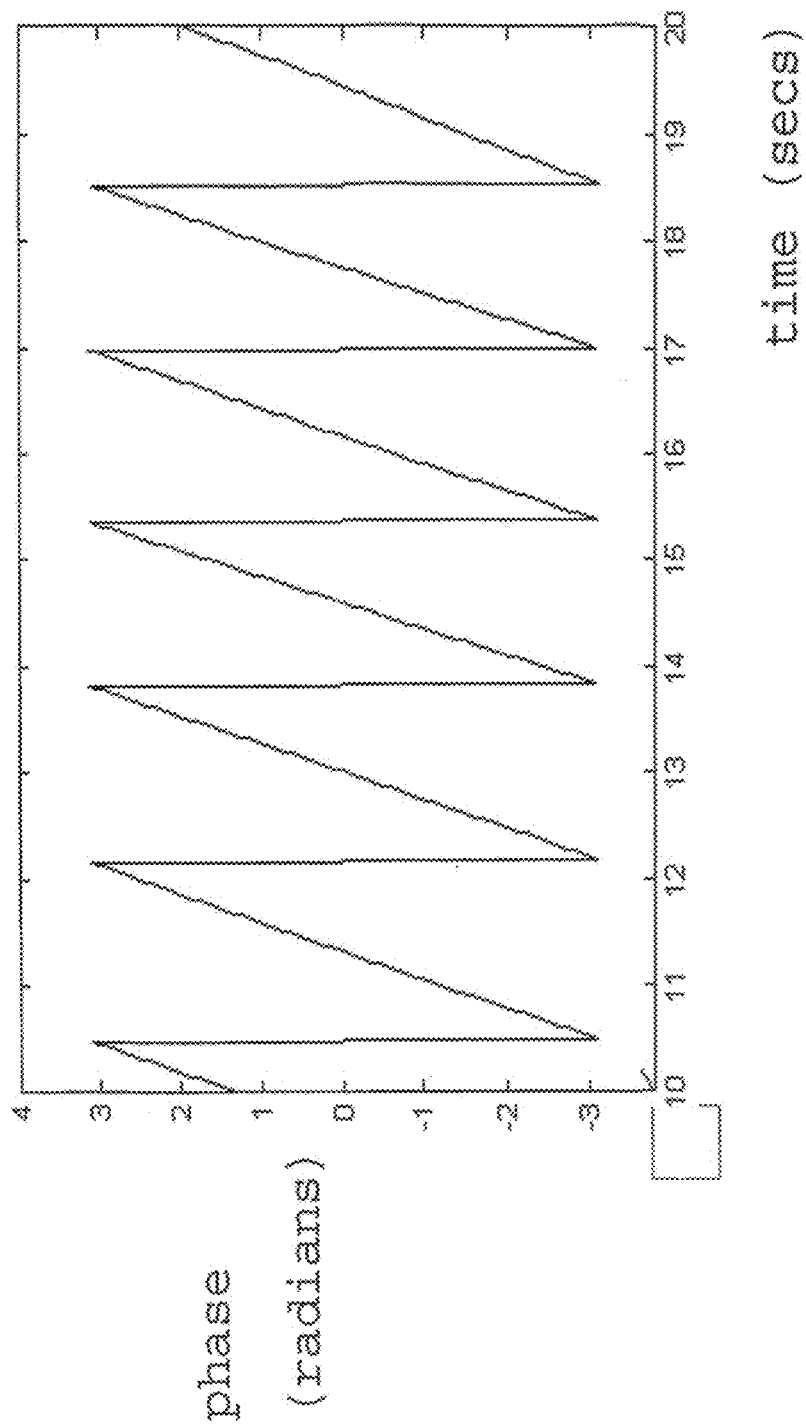
Figure 10:
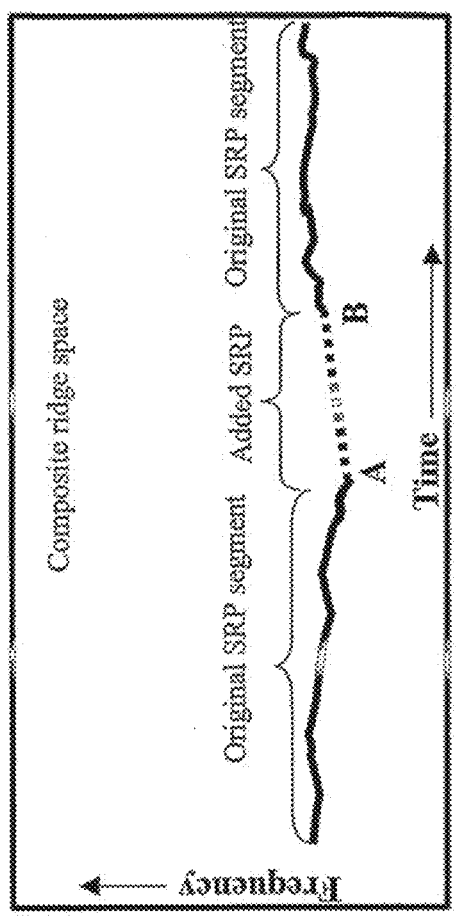

The selected ridge path (SRP) is then used to provide an overall confidence as to breathing rate and/or provide individual breath monitoring and/or prediction. By superimposing the SRP shown in FIG. 8(d) onto the phase information, derived from the original transform the phase along the SRP can be determined as shown in FIG. 9. In this way individual breaths may be identified through the behaviour of the phase cycling. This phase information along the SRP path may used to derive a breathing signal either by displaying the phase information as shown in FIG. 9 or by taking the cosine, or similar function, of the phase information to produce a sinusoidal waveform, or by some other method to provide a waveform of choice for visual display of the breathing signal. In an alternative embodiment the phase information from one of the secondary transforms or a combination of the phase information from all transforms may be used in the method. In addition, the phase information used may be processed to remove erroneous phase information for example caused by movement artifact.

Parts of the SPR may contain missing segments caused by, for example, signal artefact. In these regions the SRP may be inferred using the last available path point and the next available path point as shown schematically in FIG. 10. In the preferred embodiment this is carried out using a linear fit between the points. However, other methods may also be used without departing from the scope of the invention.

3.3 Oxygen Saturation Measurement

The amplitude of signal features scale with their wavelet transform representation. Thus by dividing components of the wavelet transform of the red PPG signal toy those of the infrared PPG signal we obtain new wavelet-based representations which contain useful information on the signal ratios for use in the determination of oxygen saturation. If a complex wavelet function is used this information may be extracted using a suitable path defined on the ratio of the moduli of the transforms or using a Lissajous plot from the real or imaginary parts of the transforms. If a wavelet function containing only a real part is employed then this information should be extracted using a Lissajous plot derived from the transforms. Two complimentary methods for the extraction of the wavelet-based ratio information required for the determination of oxygen saturation are given below.

Figure 11:
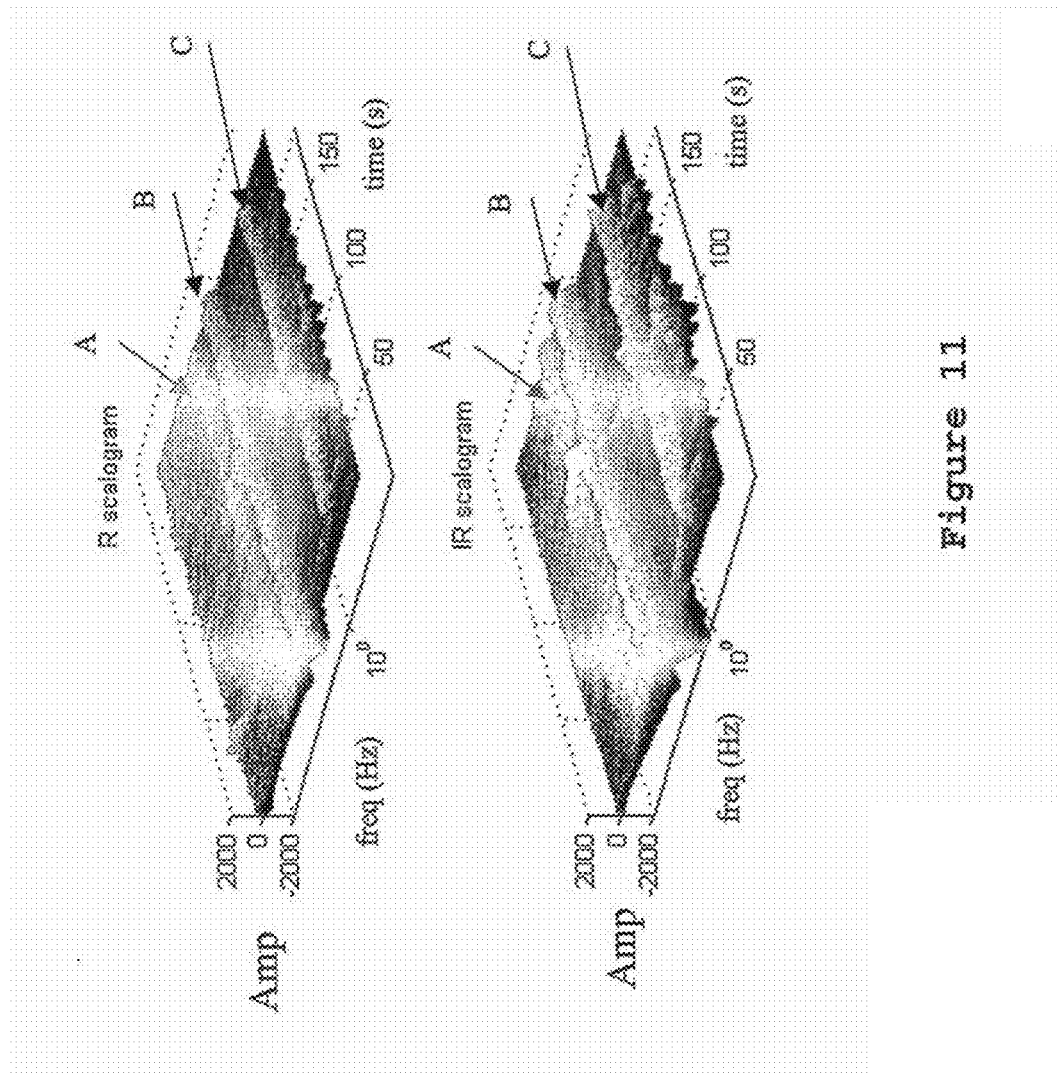

FIG. 11 shows the three dimensional plots of the real-parts of the wavelet transforms of the simultaneously collected red and infrared. PPG signals. A complex Morlet wavelet was used in the transform. The dominant nature of the pulse band and breathing band regions is evident in the figure. These are marked 'B' and 'C' respectively in the figure. A secondary band containing pulse components can also be seen in the figure (marked 'A'). This band is associated with the double humped morphology of the PPG waveform. In the new wavelet-based Lissajous method a number of frequency levels are selected within a moving window. The moving window is shown schematically on the plot in FIG. 12, (Here we use a 4.56 second window for the purpose of illustration although alternative window lengths may be used as required.) The oscillatory nature of the pulse band and breathing band regions is evident in the plot. The wavelet transform values along each of these frequency levels for the red and infrared signals are plotted against each other to give a Wavelet-Based Lissajous (WBL) plot. This results in a multitude of WBL plots, one for each frequency level selected. In the method, the selected frequency levels lie in the range of expected pulse frequencies which is, for the purposes of illustration, herein defined as between 0.67 and 3.33 Hz. This range may be altered to reflect the application. The multitude of WBL plots may be displayed together to form a 3-D Lissajous figure, as shown in FIG. 13(a).

Note that, in the example shown here, a complex wavelet function was used and hence both real or both imaginary values of the transform can be utilised in the method. Further, information from the real WBL plots and imaginary WBL plots may be combined to provide an optimal solution. If a real-only wavelet function is used (i.e. a wavelet function containing only a real part and no imaginary part) than only one set of transforms (real) are available to use.

Figure 13:
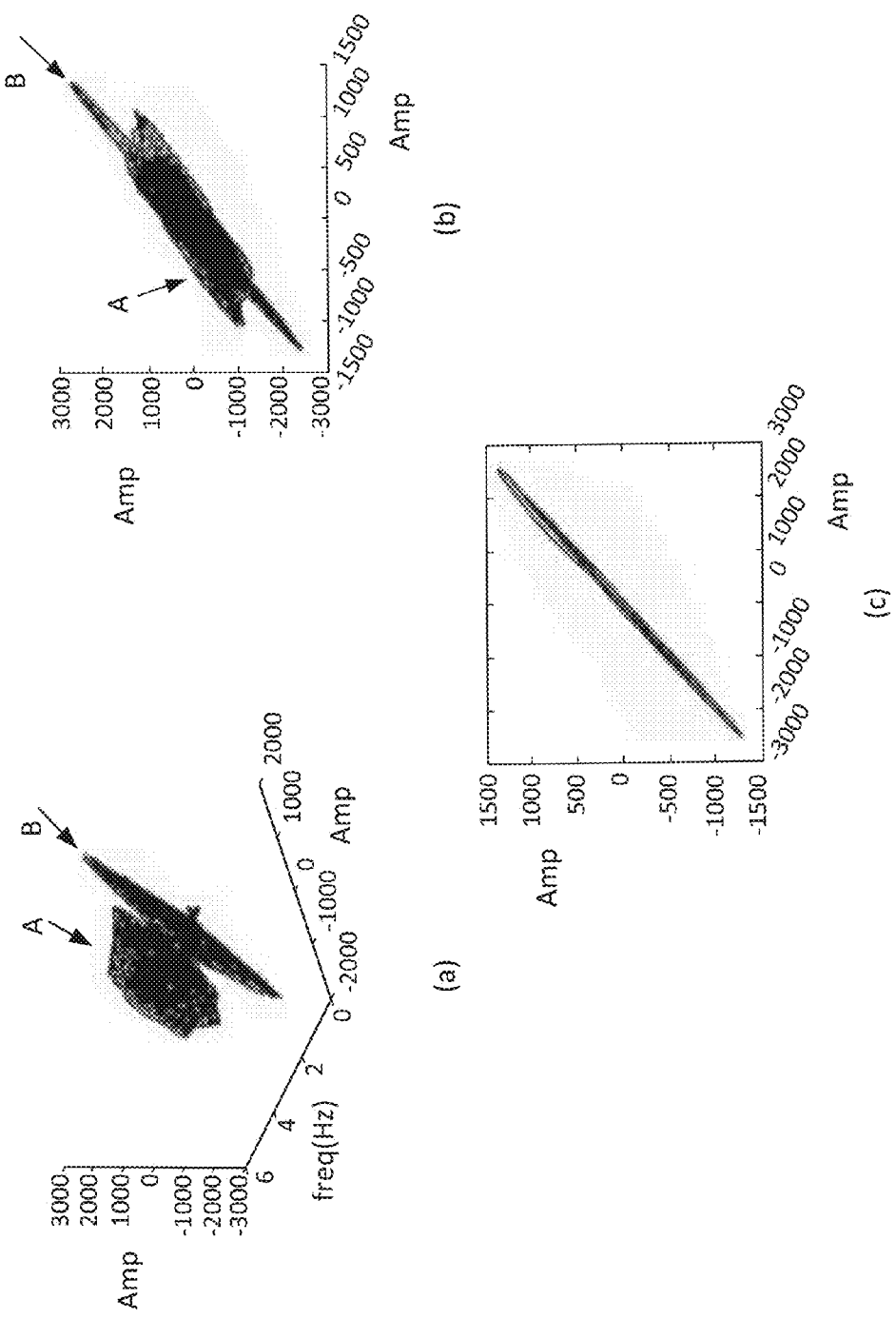
Figure 14:
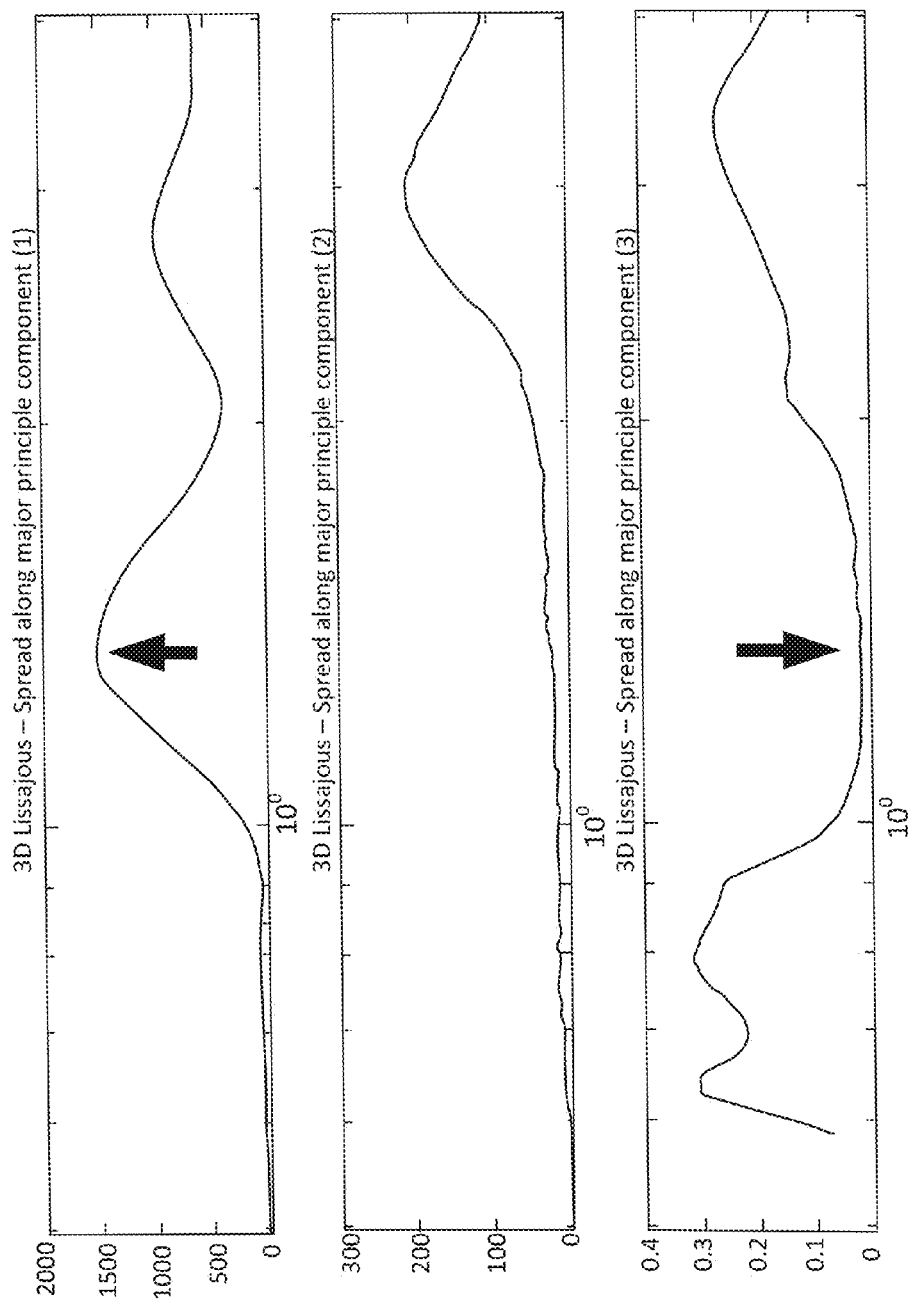

Each Lissajous plot making up the 3-D Lissajous figure is then probed to find its spread both along its principle axis and that axis orthogonal to it. To do this, any reasonable measure of spread may be used. Here we employ the standard deviation (SD). FIG. 13(b) shows an end on view of the 3-D Lissajous of FIG. 13(a). The region of the 3-D Lissajous FIGS. 13(a) and 13(b) in the vicinity of the pulse frequency is marked by the letter 'B' in the figures and higher frequencies are marked by the letter 'A'. FIG. 14 contains plots of the standard deviation of data spread along the principle axis (top plot) and minor axis (middle plot), and the ratio of the standard deviations (lower plot) for each Lissajous component making up the 3-D Lissajous plot in FIG. 13(a). In the preferred embodiment the Lissajous component with the maximum spread is used in the determination of the oxygen saturation. The location of this component is marked by the arrow in the top plot of FIG. 14. This component, with the maximum spread along the major principle axis, is plotted in FIG. 13(c): the representative slope of which is computed and used to determine the local oxygen saturation value using a predefined look-up table. This maximum spread is usually found at or near the pulse frequency. A check is also made on the SD ratios: defined as the SD of spread along the major axis divided by the SD of spread along the minor axis. A low SD ratio implies good correlation between the two signals. The SD ratio for the component with maximum spread is indicated by the arrow in the lower plot of FIG. 14. We can see for this case that a relatively low SD ratio occurs at this location. The SD ratio check may be used to pick a more appropriate wavelet-based Lissajous plot and can form part of a noise identification and/or reduction algorithm. Alternate methods of picking an optimal wavelet-based Lissajous may also be employed as appropriate. During periods of excessive noise, the Lissajous components can become spread out in shape, and in some cases the direction of the major and minor principle axis can significantly change from that of the relatively noise free portions of the signals. A check can therefore be made to determine if this has occurred by retaining a recent history of the selected Lissajous components. This can further be used as a confidence check on the selected Lissajous figure used in the determination of oxygen saturation.

Note that the ratio of the amplitudes of the independent wavelet signals making up the selected Lissajous component may also be used to determine the oxygen saturation. Note also that the inverse transform of these wavelet signals may be used in the method to determine oxygen saturation. The method described can be used to extract the pertinent ratio information from wavelet transforms computed using either complex or real-only wavelet functions.

Figure 15:
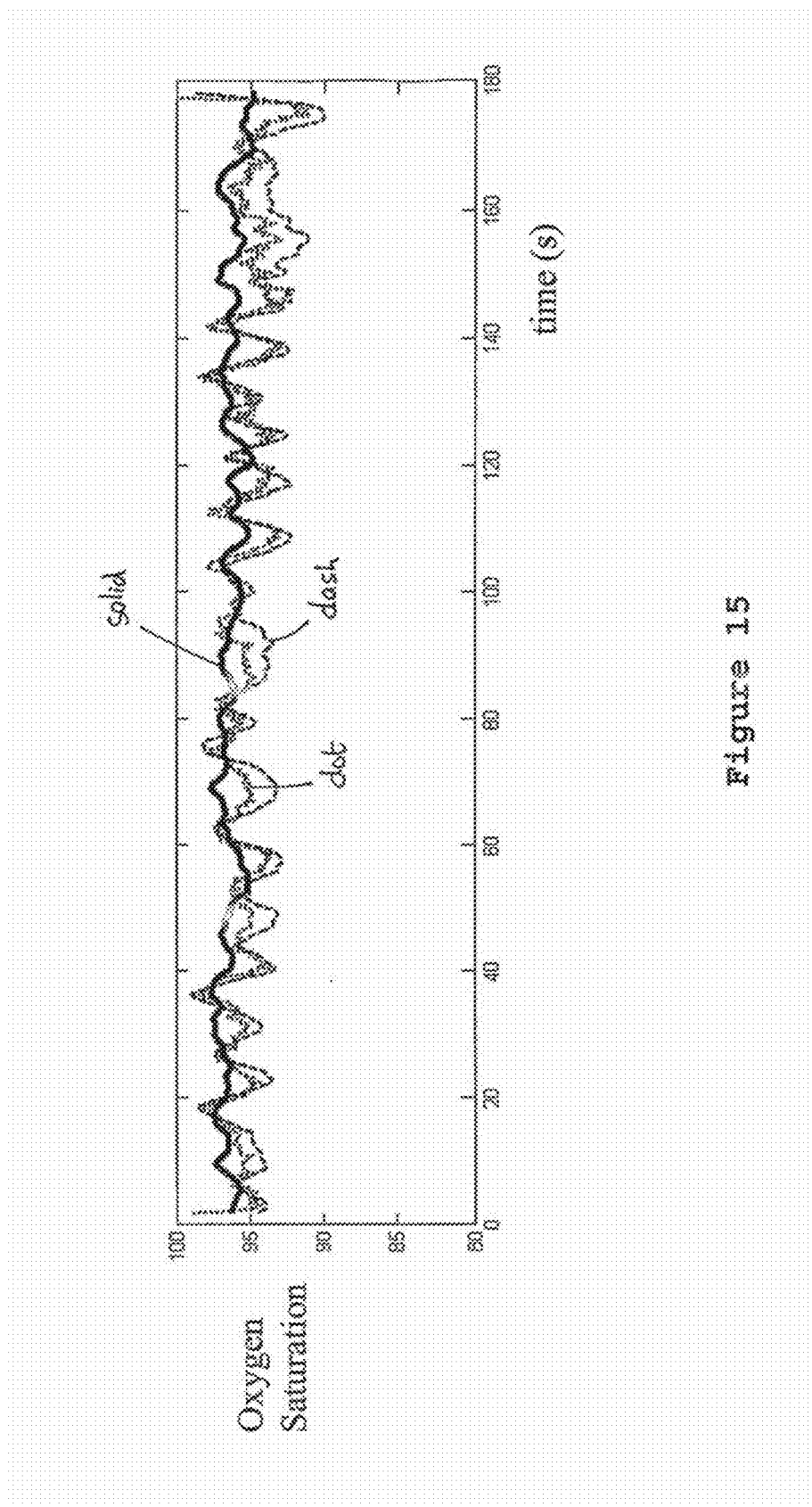

FIG. 15 shows the oxygen saturation determined using the 3-D Lissajous method (solid black line) compared with the traditional signal amplitude method (dotted) and signal Lissajous method (dashed). All three methods employed a 4 second smoothing window. It can be seen that for the particular example signal interrogated here (the signals taken from the finger of a healthy male patient aged 42 sitting in an upright position at rest) the wavelet method produces a more consistent value.

Figure 16:
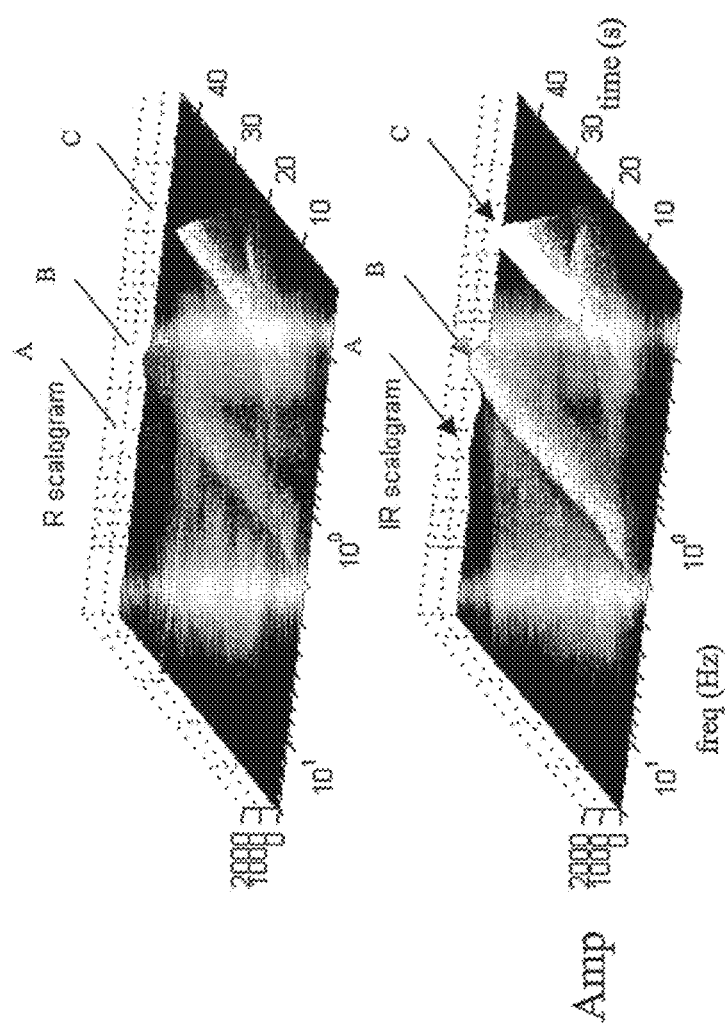

FIG. 16 contains three-dimensional views of the red and infrared scalograms corresponding to an example PPG signal. Here the modulus of the complex transform is used. The locations of the band associated with the pulse component are indicated in the plots (denoted 'B' in the figures). We define the collection of points corresponding to the path of the maxima of the band projected onto the time frequency plane as P. A wavelet ratio surface ($R_{WT}$) can be constructed by dividing the wavelet transform of the logarithm of red signal by the wavelet transform of the logarithm of the infrared signal to get a time-frequency distribution of the wavelet ratio surface, i.e.

$$R_{WT} = \frac{|T(a,b)_R|}{|T(a,b)_{IR}|} \quad [7]$$

where where the subscripts R and IR identify the red and infrared signals respectively. The wavelet ratio surface derived from the two scalograms in FIG. 16 is shown schematically in FIG. 17. Note that as described previously in our definition of scalogram we include all reasonable forms of rescaling including the original unsealed wavelet representation, linear resealing and any power of the modulus of the wavelet transform may be used in the definition. As the amplitude of the wavelet components scale with the amplitude of the signal components then for regions of the surface not affected by erroneous signal components the wavelet ratio surface will contain values which can be used to determine the oxygen saturation using a pre-defined look-up table.

Figure 17:
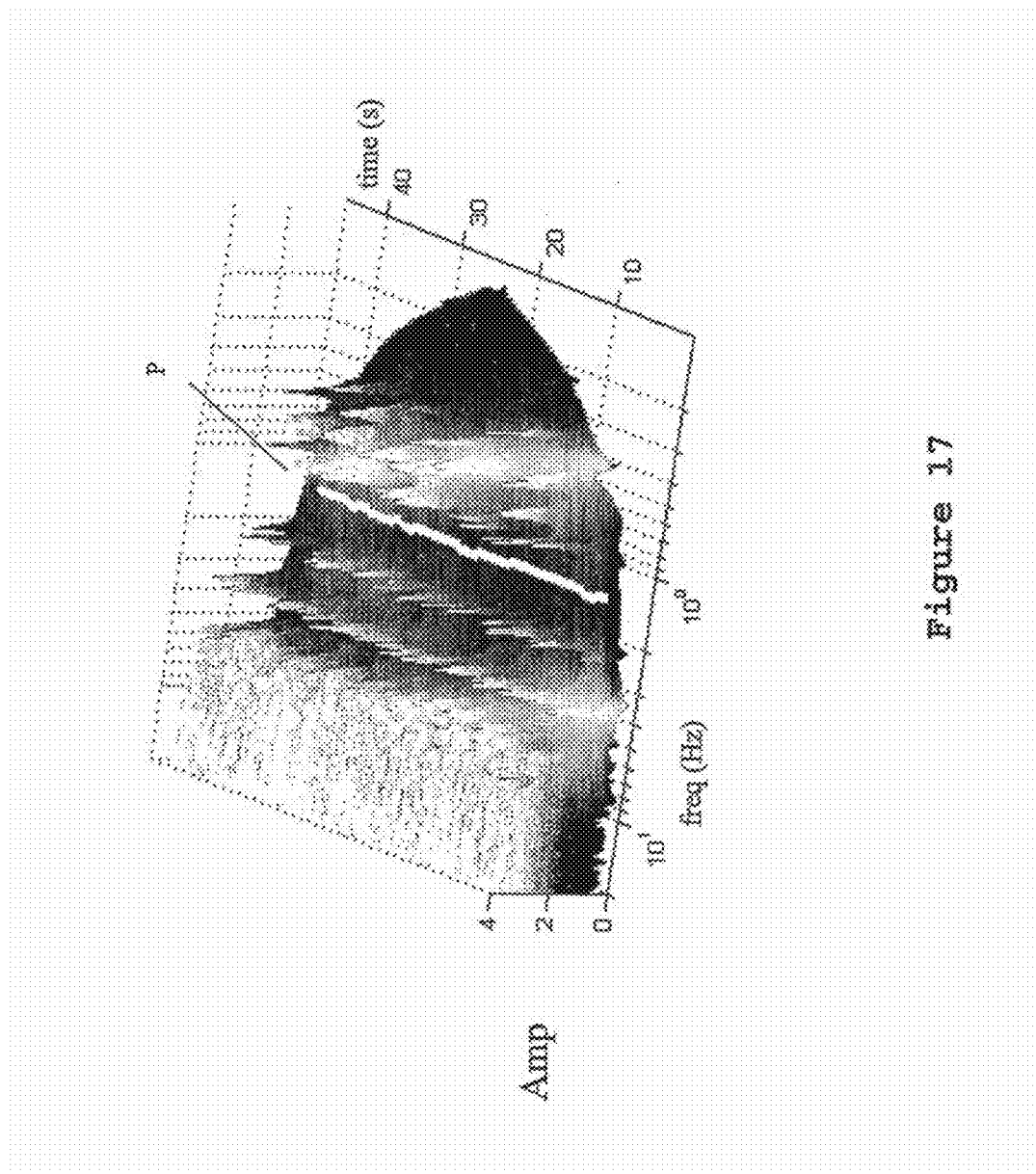

As can be seen in FIG. 17, the time frequency wavelet ratio surface along, and in close proximity to, the projection of the pulse ridge path P onto the wavelet ratio surface are stable and hence may be used in the robust determination of the oxygen saturation. In the preferred embodiment the values obtained along the projection of P onto $R_{WT}$ are used to determine oxygen saturation via a pre-defined look-up table which correlates $R_{WT}$ to oxygen saturation.

A 2-D or 3-D view of the $R_{WT}$ plot may be computed and displayed in real time to provide a visual indication of the quality of the ratio of ratios obtained by the method, and hence the quality of the measurement of oxygen saturation.

Figure 18:
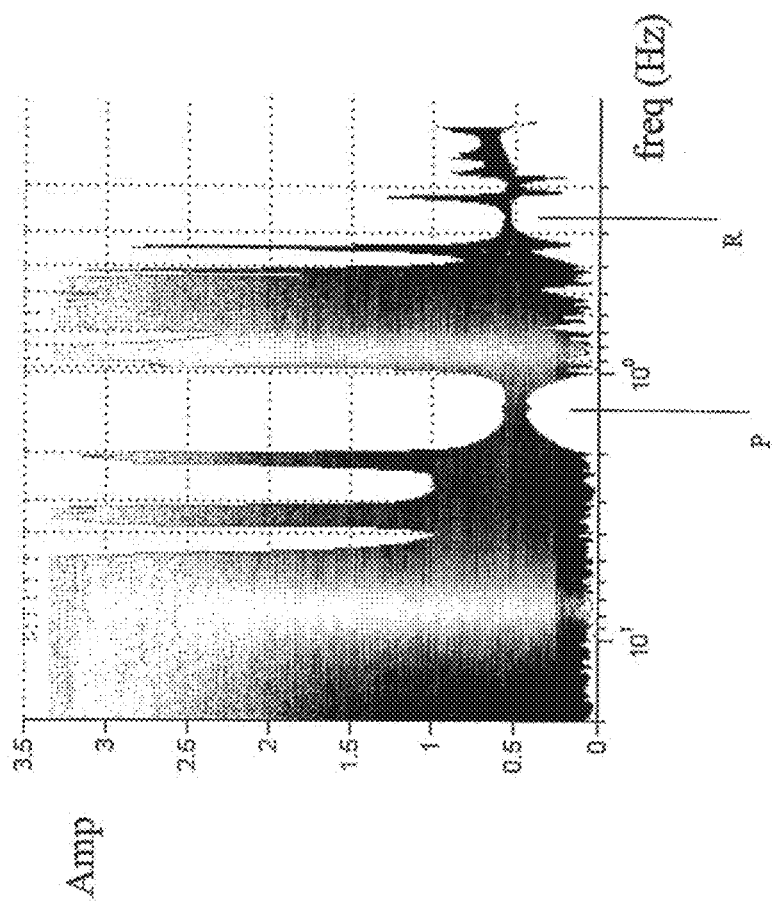

FIG. 18 contains a plot of the end view of the wavelet ratio surface shown in FIG. 17. From the figure we see that a relatively stable, flat region is also found at or near the respiration frequency (R in the figure). It has bean noted from experimentation that for some cases the respiration region of the wavelet ratio surface may lie at a different level from the pulse band region. Hence, for these cases, using $R_{WT}$ obtained in the breathing region would produce erroneous values of oxygen saturation. By following a path in the region of the pulse band our method automatically filters out erroneous breathing components in the signal.

Figure 19:
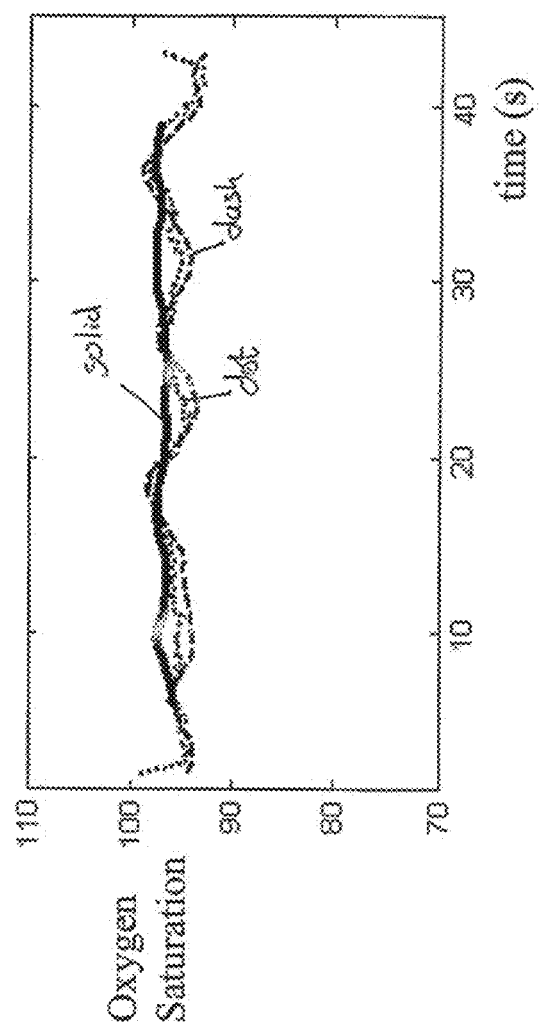

FIG. 19 contains a plot of the oxygen saturation determined by the wavelet ratio surface method as a function of time as compared with two standard methods: the traditional signal amplitude method and the traditional Lissajous method. The PPG signals were again taken from the finger of a healthy male patient aged 42 sitting in an upright position at rest. From visual inspection of the plot it can be seen that, for this example, the wavelet-based method produces a more consistent value of oxygen saturation compared to contemporary methods.

It will be recognized by those skilled in the art that, in an alternative embodiment, the pulse band ridge path P can also be projected onto the real or imaginary transform components. From the values of the transform components along this path over a selected time interval a Lissajous figure may be obtained and used in the determination of oxygen saturation. It will also be recognised by those skilled in the art that, in an alternative embodiment, alternative paths may be projected onto the wavelet ratio surface and used for the determination of oxygen saturation. For example in regions where the pulse band exhibits noise causing the path of the ridge maxima to move far from the actual pulse frequency a method for detecting such noisy events and holding the path to the most appropriate recent pulse frequency may be used until the event has passed or until a preset period of time whereby an alarm is triggered.

The 3-D Lissajous and wavelet ratio surface methodologies for the determination of oxygen saturation, as described, above, can form the basis of an algorithm for incorporation, within pulse oximeter devices. Furthermore the ability of the methodologies to restrict themselves to the optimal wavelet transform values by picking the optimal Lissajous or following the pulse band respectively, allows for erroneous signal, elements to be discarded automatically; so leading to a more robust algorithm for the determination of oxygen saturation.

Note that in both new methods the inverse transform of the selected wavelet values may also be use, as they too scale with the signal features.

In the preferred embodiment, both the 3-D Lissajous and wavelet ratio surface methods are employed simultaneously and the optimal measured saturation value determined. It is obvious from the above description that the initial inputted signals and wavelet transformation of these signals form common elements to tooth methods.

Those skilled in the art will recognise that modifications and improvements can be incorporated to the methodology outlined herein without departing from the scope of the invention.

Those skilled in the art will recognise that the above methods may be performed using alternative time-frequency representations of the signals where the amplitude in the time-frequency transform space can be related to the amplitude of pertinent features within the signal. However, in the preferred method the continuous wavelet transform is employed.

In summary a method for the decomposition of pulse oximetry signals using wavelet transforms has been described which allows for underlying characteristics which are of clinical use to be measured and displayed. These wavelet decompositions can then be used to:

(a) provide, using information derived from the signal wavelet transforms (i.e. from the original transform, the repealed wavelet transforms, the ratio of derived wavelet transforms, the scalograms, wavelet ridges, etc.) a method for measuring oxygen saturation.
(b) construct, using information derived from the wavelet transform (i.e. from the original transform, the rescaled wavelet transforms, the ratio of derived wavelet transforms, the scalograms, wavelet ridges, etc.), a plurality of wavelet-based Lissajous figures from which the optimum Lissajous representation is chosen using preset criteria and the slope of which is used to determine the oxygen saturation of the signal using a look-up table.
(c) construct, using information derived from the wavelet transform (i.e. from the original transform, the resealed wavelet transforms, the ratio of derived wavelet transforms, the scalograms, wavelet ridges, etc.), a time-frequency equivalent of the ratio of ratios, the wavelet ratio surface, from which to determine the oxygen saturation of the signal toy following a selected path through the time frequency plane. The preferred path through the time frequency plane to be that corresponding to the pulse band.
(d) provide an optimal oxygen saturation value from those derived in (b) and (c).

3.4 The Monitoring of Patient Movement

Current devices are configured to remove detrimental movement artifact from the signal in order to clean it prior to determination of the clinical parameter of interest, e.g. the pulse rate or oxygen saturation. However, the method described herein as embodied within a device monitors general patient movement, including large scale body movements, respiration and the beating heart. In this way the absence of patient movement and/or irregularity of movement can be detected and an alarm triggered.

Figure 20:
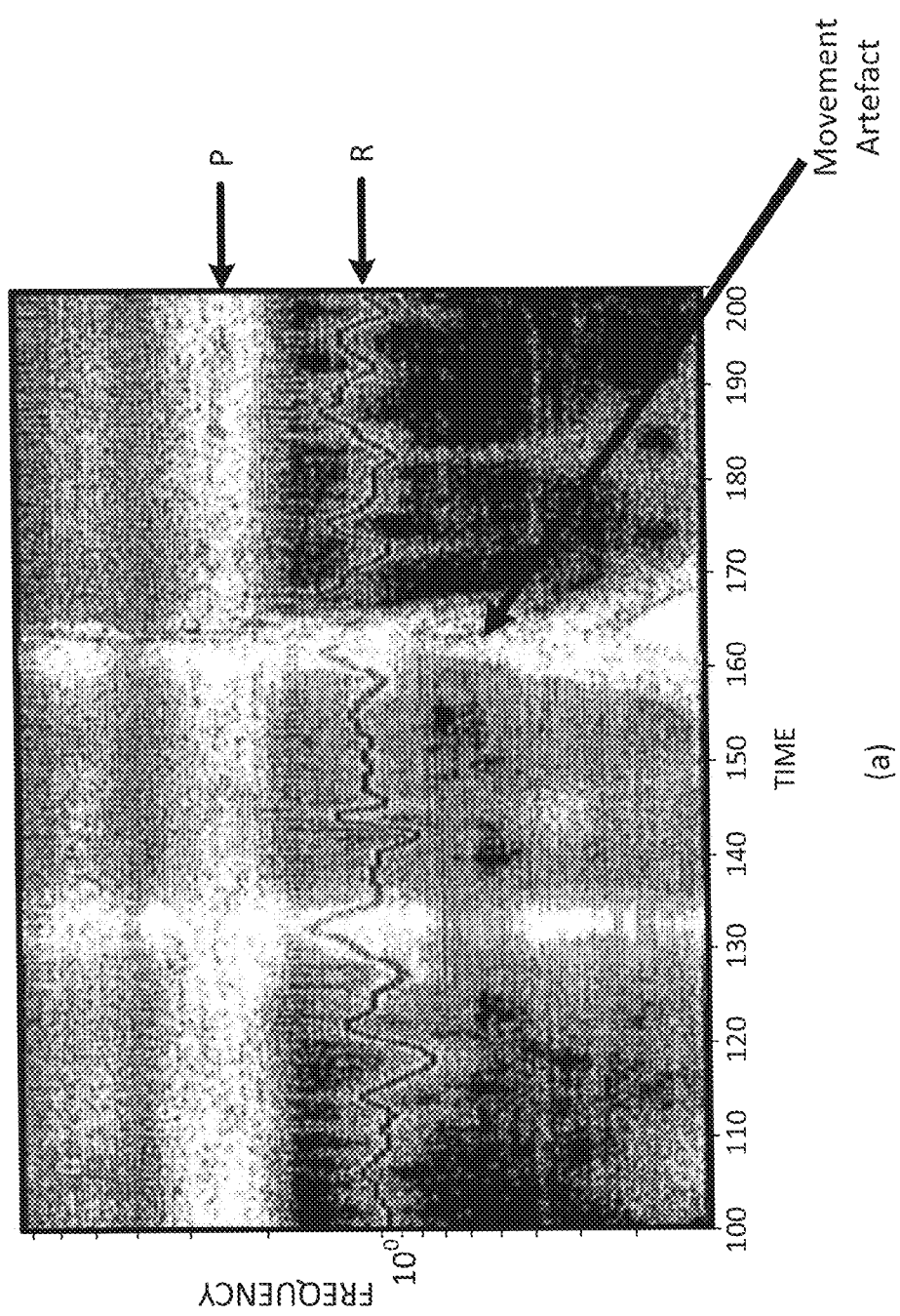
Figure 20:
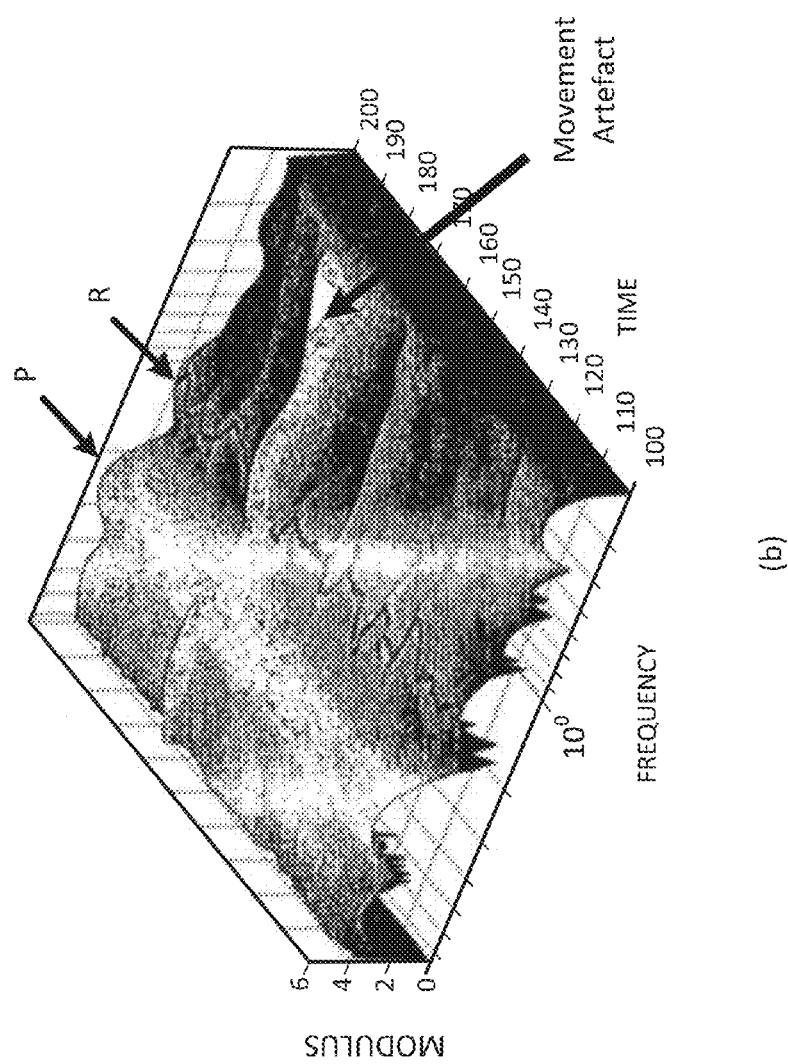

Patient movement results in PPG signal artifact. The manifestation of this artifact can be observed in the wavelet transform of the signal. An example of a movement artifact in the scalogram is shown in FIG. 20(a). The PBS signal from which the wavelet plot was derived was acquired from a premature baby a few weeks after birth. The location of the movement artifact is marked by the arrow in the plot. The breathing band ridge has been superimposed on the wavelet plot (marked R in the figure). The pulse band is marked P in the figure. Notice that the artifact causes a drop-out in the detected breathing ridge (i.e. a missing fragment), and also cuts through the pulse band where it can cause similar drop outs to occur in the detection of the pulse ridge. It has been the focus of pulse oximeter device manufacturers to remove as much of the movement artifact component from the signal while leaving the information necessary to obtain accurate oxygen saturation and pulse rate measurements. In a preferred embodiment of the methods described herein we extract a movement component from the PPG signals for use in the monitoring of patient movement and, in particular, for the monitoring of the movement of infants.

A three-dimensional view of the scalogram of FIG. 20(a) is plotted in FIG. 20(b). Here we see the dominance of the movement artifact feature in wavelet space. By identifying such features we can monitor patient movement. It is common for young babies to exhibit very variable respiration patterns and to cease breathing for short periods of time, especially when making a movement of the body. Hence inspecting the derived movement signal when an irregular respiration signal occurs, including cessation of breathing, gives a further measure of patient status.

Figure 21:
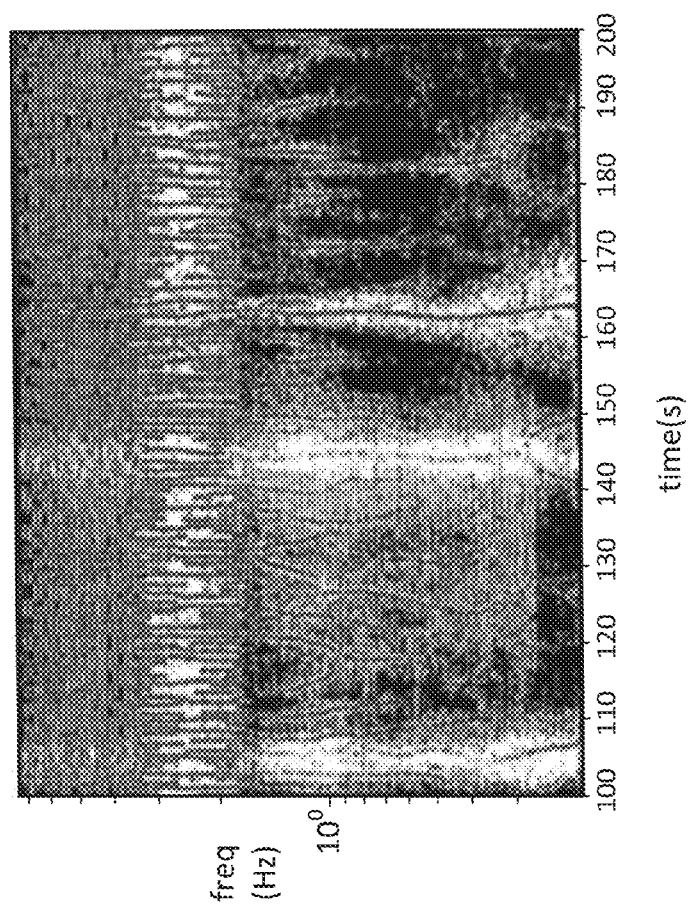
Figure 21:
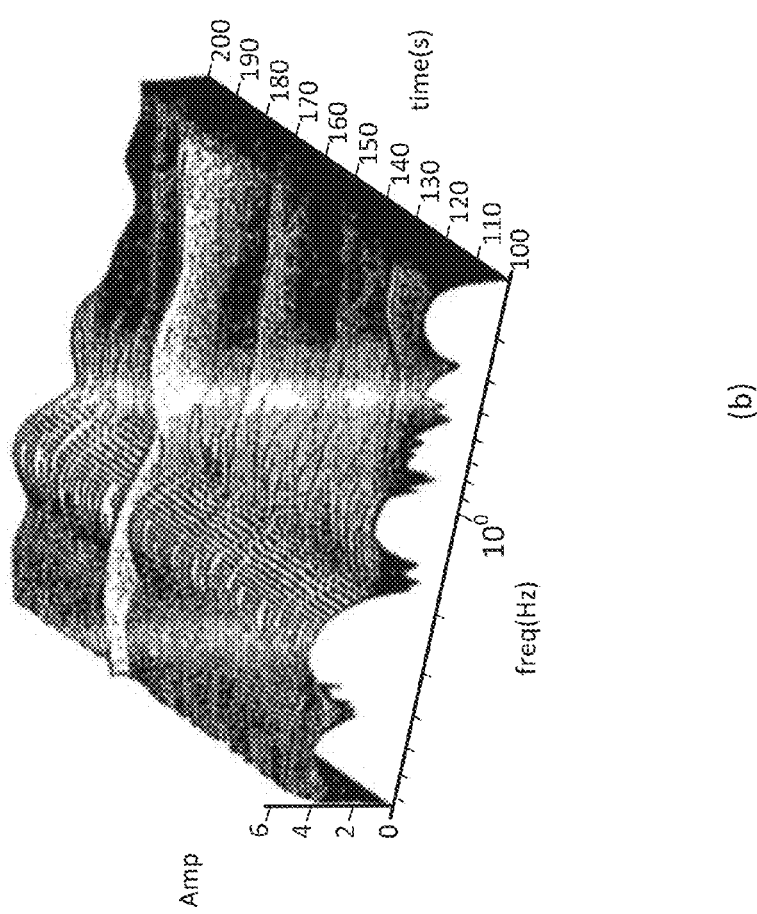
Figure 22:
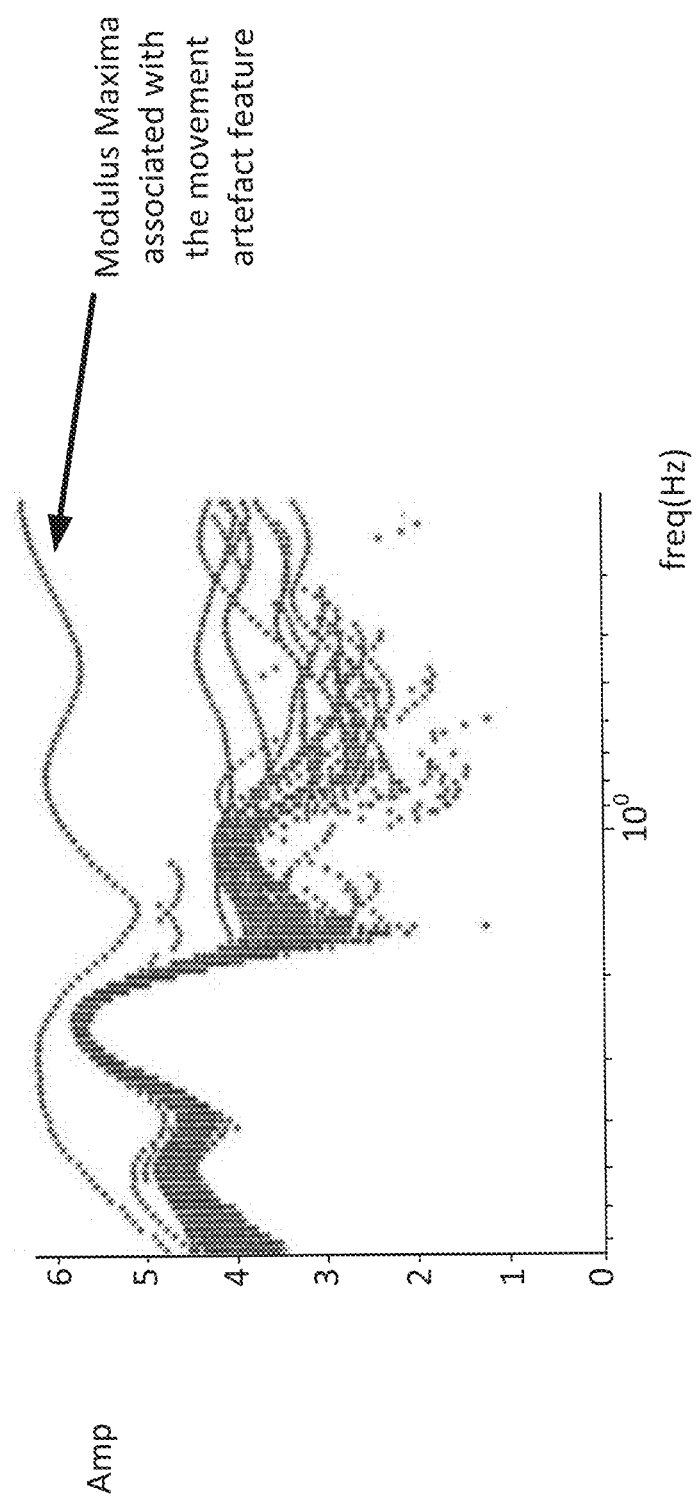
Figure 22:
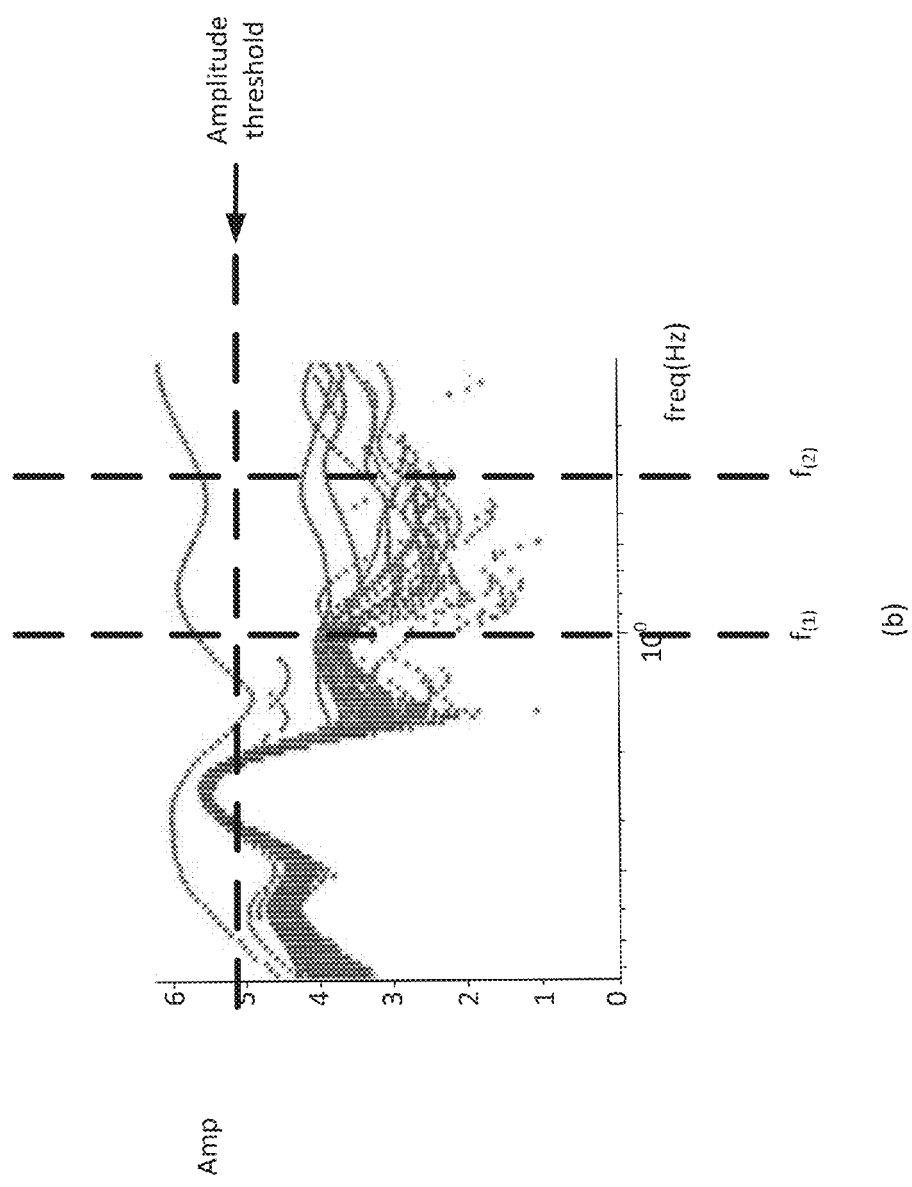
Figure 22:
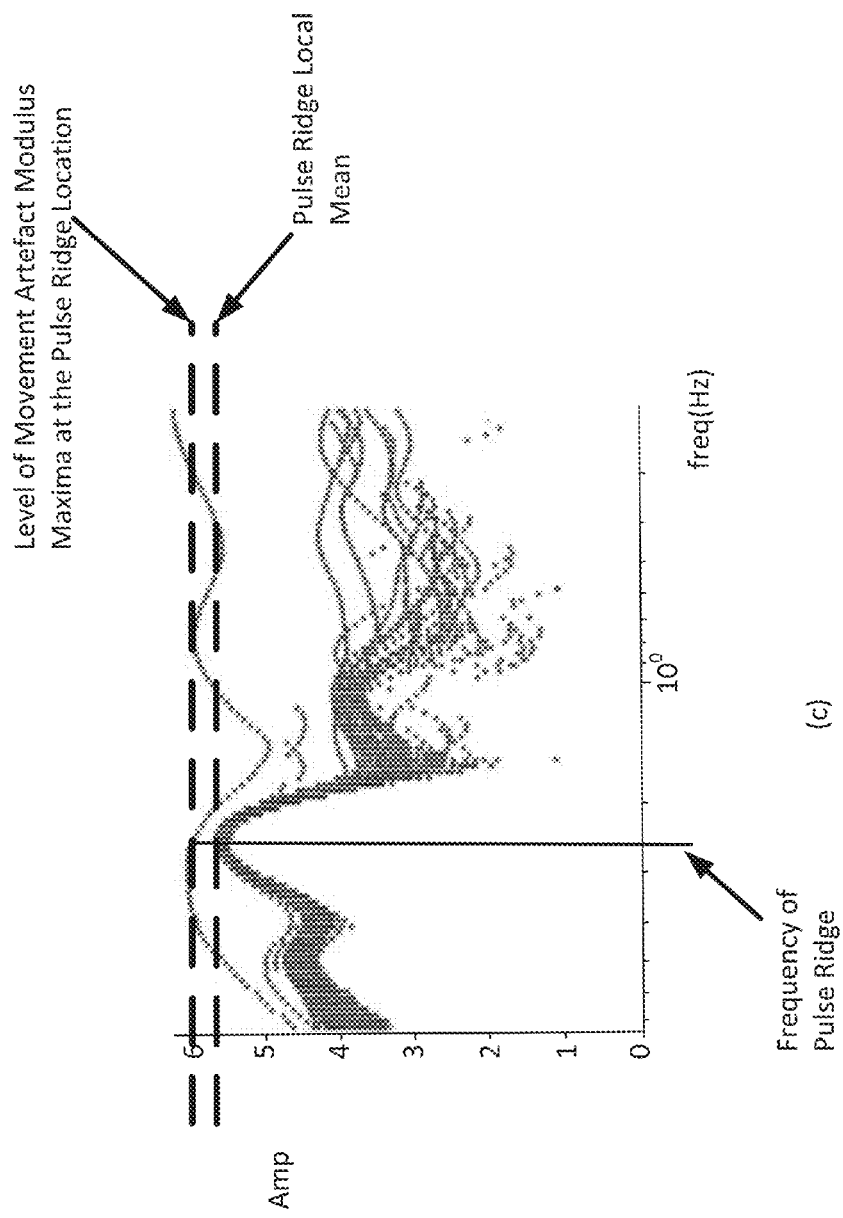
Figure 22:
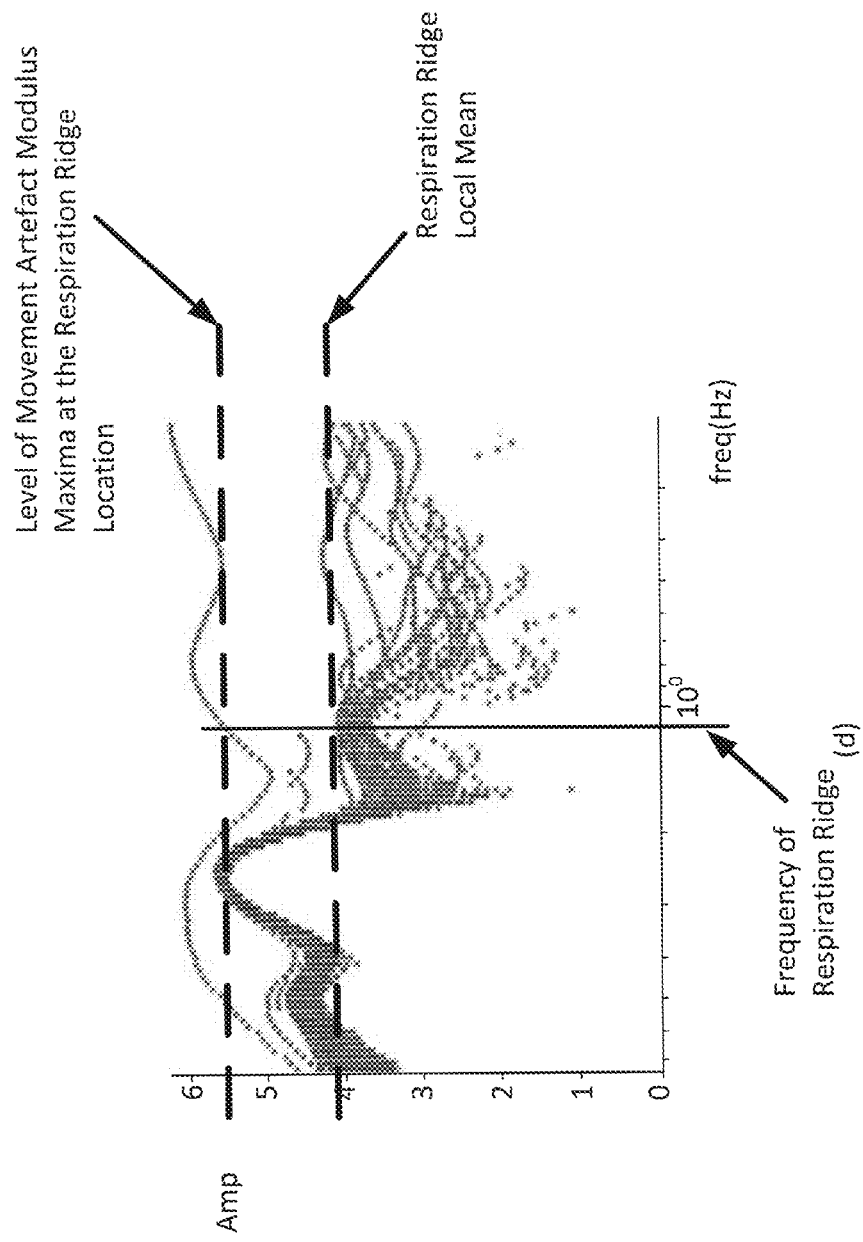

The modulus maxima of the wavelet surface is the loci of the maxima of the wavelet surface with respect to time. FIG. 21(a) plots the modulus maxima lines associated with FIG. 20(a). FIG. 21(b) shows a three-dimensional view of the transform surface with the modulus maxima lines superimposed. FIG. 22(a) shows an end view of the maxima lines (without the surface shown) corresponding to those shown in FIGS. 21(a) and 21(b). We can see from the end view that the modulus maxima line corresponding to the movement artifact has a significantly different morphology to the other maxima lines: it covers a large frequency range and contains significantly more energy than the other maxima, especially at low frequencies. By setting amplitude threshold criteria at a frequency or range of frequencies we can differentiate the modulus maxima of the artifact from other features. An example of this is shown schematically by the threshold level and frequency range depicted on FIG. 22(b), where maxima above the pre-defined amplitude threshold within a frequency range given by $f_{(1)} < f < f_{(2)}$ are identified as corresponding to movement artifact. In addition a check of local anomalies in the detected pulse and breathing ridges may also be made. For example modulus maxima which are at significantly higher amplitudes than the pulse ridge mean value in their vicinity are deemed to correspond to movement artifact. This is depicted in FIG. 22(c). In addition, modulus maxima which are at a significantly higher amplitude than the respiration ridge mean value in their vicinity are deemed to correspond to movement artifact. This is depicted in FIG. 22(d).

A region in the time frequency plane within the support of the wavelet is then deemed to contain artifact. The support of the wavelet is taken as a predefined measure of temporal 'width' of the wavelet. For wavelets with theoretical infinite width, such as the Morlet wavelet, the width is defined in terms of the standard deviation of temporal, spread: for example we use three times the standard deviation of spread each side from the wavelet centre. Thus a cone of influence of the artifact may be defined in the transform plane.

Using the above method we can monitor patient movement by detecting modulus maxima corresponding to movement artifact. This information can be used to monitor patient movement and/or to provide a measure of confidence on the derived values of other measurements (e.g. oxygen saturation, pulse and respiration). These measurements may, for example be held at a previous value until the detected movement event has passed.

Other artefact may exist in the signal which may originate from the drive and control electronics including, but not limited to, automatic gain adjustments. The occurrence of this type of artifact will be known and can be accounted for in the signal and hence differentiated from movement artifact.

4. DEVICE CONFIGURATION AND USAGE

The device may be used to monitor one or more of the following signals: respiration, pulse, breathing and movement. Useful information regarding these signals would be displayed on the device or output in a suitable format for use.

In one embodiment the device would be used to continually monitor one or more of these signals.

In another embodiment the device would be used to monitor one or more of these signals intermittently.

4.1 Device Configuration

Detailed block diagrams of the device are provided in FIGS. 23, 24, 25 and 26.

Figure 23:
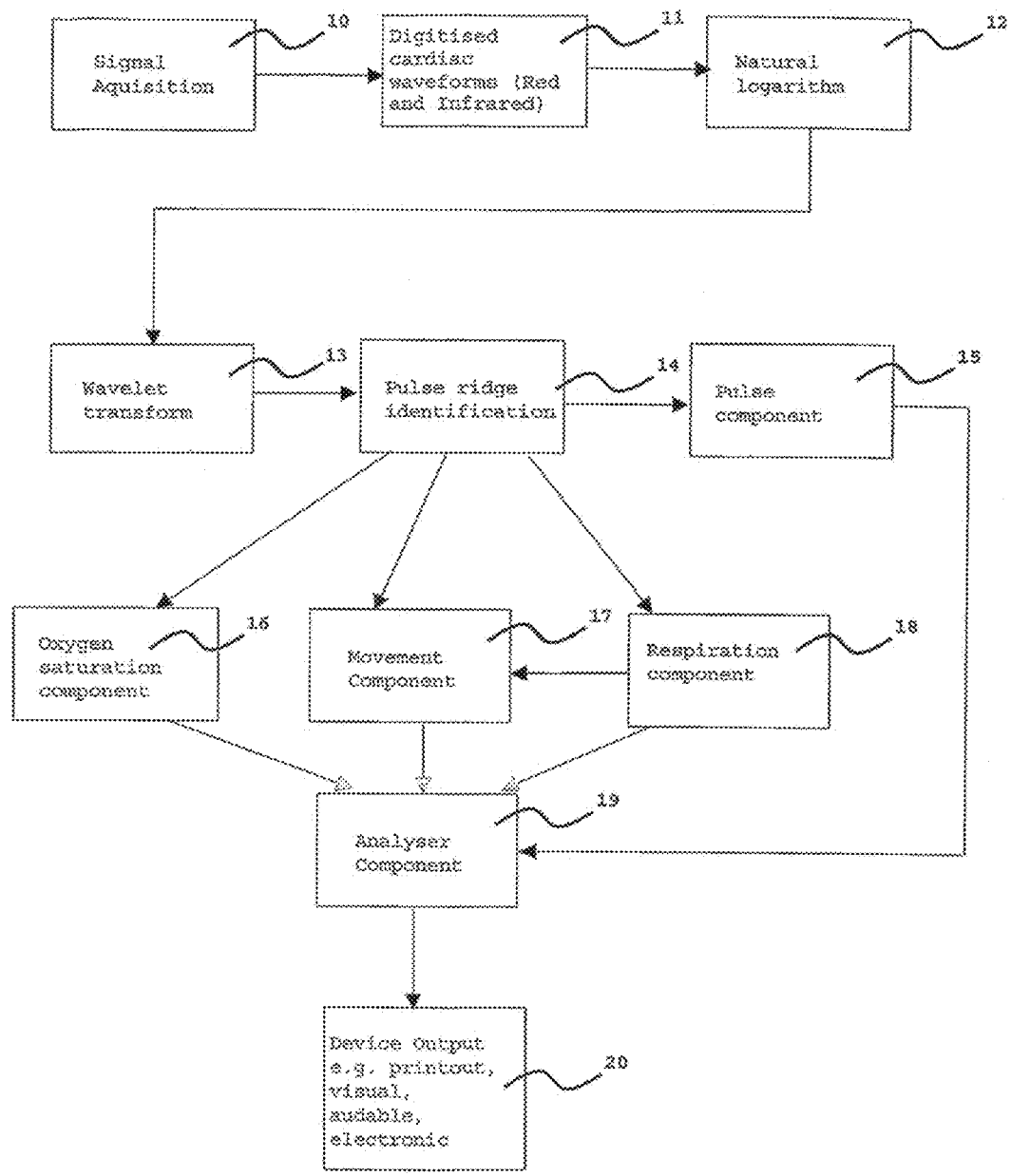

The following is with reference to FIG. 23. In the present invention signals are acquired at the patient's body 10. These are sent for digitization 11. The links between components of the system may be fixed physical or wireless links, for example radiofrequency links. In particular, either or both of the links between 10 and 11 or 11 and 12, or the links between the analyser component and a visual display may a wireless link enabled by a radiofrequency transmitter. The digitised cardiac signals 11 are sent to 12 where in the preferred embodiment the natural logarithm of the signals are computed. These are then sent to 13 where the wavelet transforms of the signals are performed. The components of the wavelet transformed signals, including modulus, phase, real part, imaginary part are then sent to 14 where the pulse ridge is identified. The information from 13 and 14 is then used in the extraction of patient pulse information 15, oxygen saturation 16, patient movement information 17 and respiration information 18. The information regarding oxygen saturation, pulse, respiration and patient movement is all sent to the Analyser component 19 where it is collected and collated ready for outputting at 20. The oxygen saturation, respiration, pulse rate and movement information is output from the device 20 through a number of methods, which may include a printout, a display screen or other visual device, an audable tone, and electronically via a fixed or remote link. The output information may be sent to a location remote from the patient, for example sent via telephone lines, satellite communication methods, or other methods. Further, real-time wavelet-based visualisations of the signal (including the original transform and/or the wavelet ratio surface with projected pulse ridge path) may be displayed on the device 20. These visualisations will highlight salient information concerning the quality of the outputted measurements. Additional useful information regarding movement artefact and breathing information may be apparent from such a real time display.

The workings of components 15, 16, 17 and 18 shown in FIG. 23 are described below in more detail.

Pulse Component 15: With reference to FIG. 23, pulse information including pulse rate and pulse irregularities are derived at 15 using the instantaneous frequency of the pulse band ridge determined at 14. The instantaneous frequency may correspond directly with the instantaneous ridge frequency or require a mapping from the instantaneous ridge frequency and the true respiration rate. Further the method allows for a smoothing of this value over a fixed time interval. Further the method allows for erroneous values of the pulse rate derived in this way to be excluded from the outputted values. This component 15 may also be used to measure inter-beat intervals and pertinent pulse wave timings. The pulse information determined at 15 is then sent to the Analyser Component 19.

Figure 24:
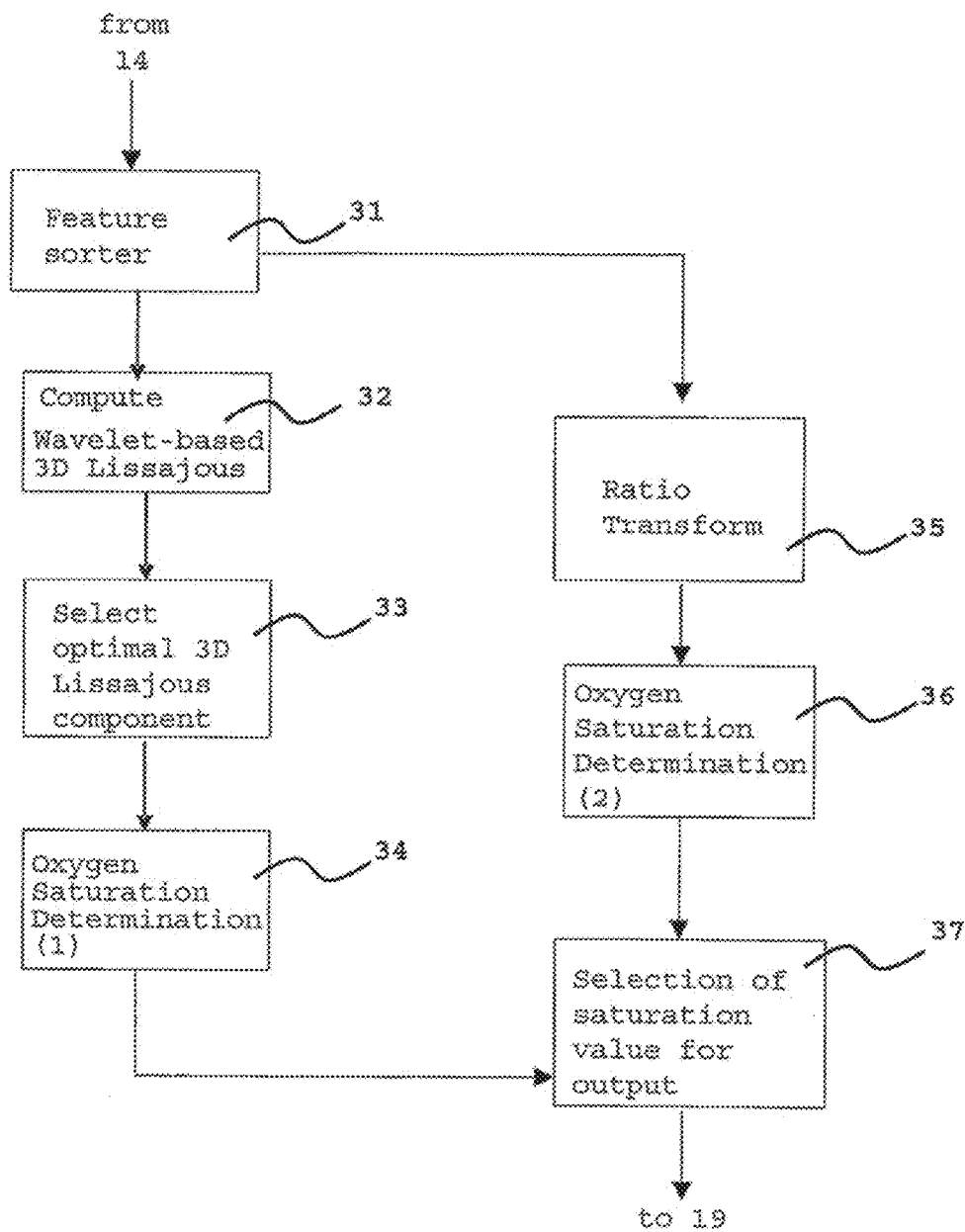

The Oxygen Saturation Component 16: The following is with reference to FIGS. 23 and 24. The oxygen saturation component 16 shown in FIG. 23 comprises the subcomponents 31, 32, 33, 34, 35, 36 and 37 as shown in FIG. 24. The wavelet transform information and pulse ridge information from 14 is input into this module at the feature sorter 31 which sends the relevant information to the Lissajous computation unit (components 32, 33 and 34) and the pulse ridge computational unit (components 35 and 36). A predetermined number of wavelet-based Lissajous are computed over the pulse region 32. An automated procedure is employed for the determination of the optimal Lissajous for use in the oxygen saturation, calculation 33. In the preferred embodiment this would be achieved by comparing the standard deviations of the data spread along of the principle axes of the Lissajous plot. The slope of the principle axis is then used to determine the oxygen saturation using a suitable look-up table which correlates the slope to oxygen saturation 34. The oxygen saturation determined at 34 is denoted 'Oxygen Saturation Determination (1)'.

The information regarding the wavelet transforms of the PPG signals and the path of the pulse ridge is collected at the feature sorter 31 used to compute the wavelet ratio surface 35. The wavelet ratio corresponding to the pulse path is determined the projecting the pulse path onto the wavelet ratio surface. This ratio is then used to determine the oxygen saturation using a look-up table which correlates the wavelet ratio to oxygen saturation 36. The oxygen saturation determined at 36 is denoted 'Oxygen Saturation Determination (2)'. The two oxygen saturation values (1) and (2) are then used to determine the most appropriate value of oxygen saturation 37. This value is then sent to the Analyser Component 19.

Figure 26:
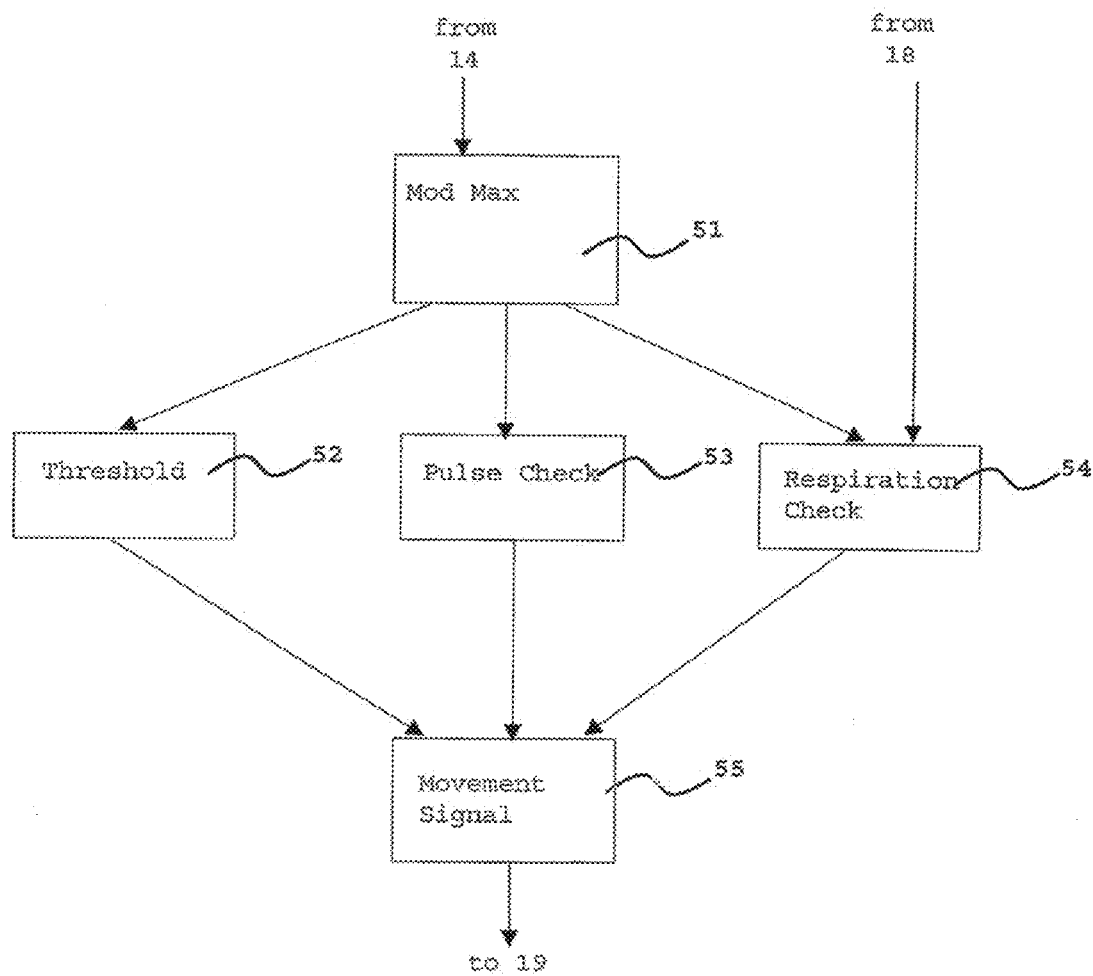

Movement Component 17: The following is with reference to FIGS. 23 and 26. The Movement component 17 of FIG. 23 comprises the subcomponents 51, 52, 53, 54, 55 as shown in FIG. 26. The wavelet transform information and pulse ridge information is sent from 14 to the modulus maxima component 51 where the modulus maxima of the wavelet surfaces are computed. The modulus maxima information is then sent to be analysed for movement artifact. The modulus maxima information is sent to the components 52, 53 and 54. These are described as follows. The Threshold component 52 detects maxima above a preset threshold and within a preset frequency range which are them defined as movement artifact. The Pulse Check component 53 checks the maxima corresponding to the pulse band to see if anomalously large excursion from the local mean level has occurred. If so movement artifact is detected. The Respiration Check component 54 checks the maxima in the vicinity of the selected respiration path SRP obtained from 18 to determine if anomalously large excursion from the local mean level has occurred. If so movement artifact is detected. The information from components 52, 53 and 54 are then collected and collated at the Movement Signal component 55 where a movement signal is generated. This is then sent to the Analyser Component 19.

Figure 25:
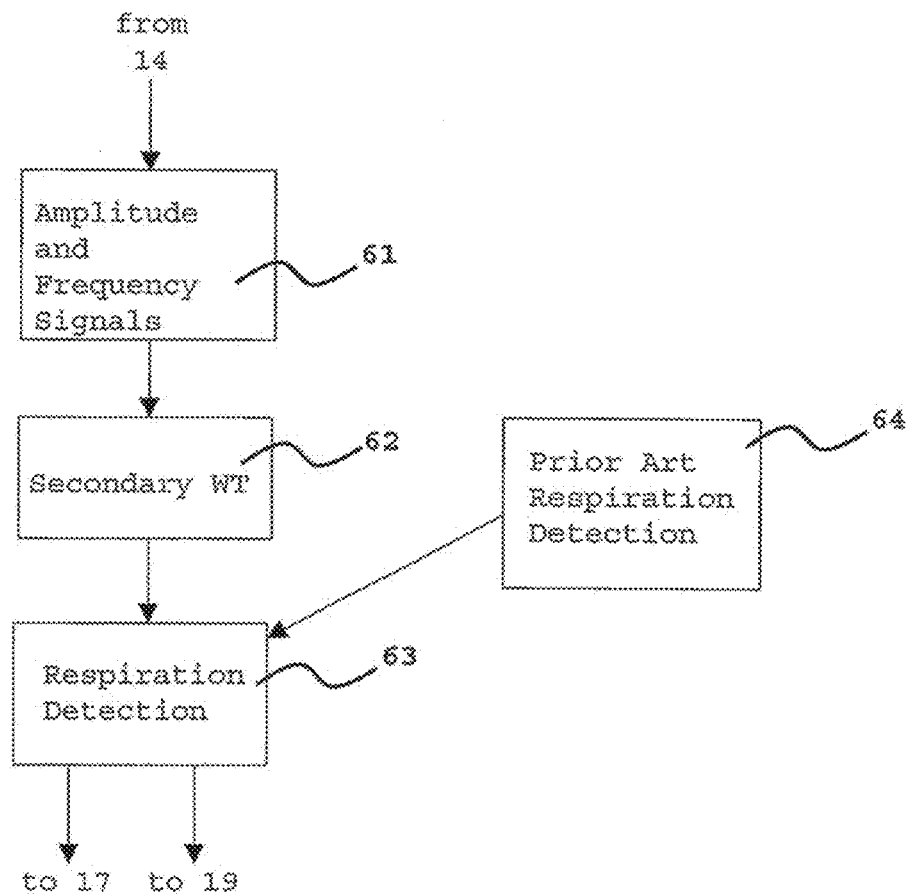

Respiration Component 18: The following is with reference to FIGS. 23 and 25. The respiration component 17 of FIG. 23 comprises the subcomponents 61, 62, 63 and 64 as shown in FIG. 25. The wavelet transform and pulse ridge information from 14 are input into this module at component 61 which uses the information to derive the ridge amplitude perturbation (RAP) signal and the ridge frequency perturbation (RFP) signals. The RAP and RFP signals are derived using the path defined by the projection of the maxima of the pulse band or a locus of points displaced from this maxima path. A secondary wavelet transform is performed on these signals 62 and then, passed to the respiration detection component 63 where the respiration ridges are detected for the wavelet transforms of the RFP and RAP signals. These are used within an algorithm which decides the selected respiration path (SRP). This algorithm may also incorporate respiration information using complementary methods 64. Note that in the method the original transform obtained at 13 and the secondary transform 62 may be computed using different wavelet functions. The respiration information is then seat to the Analyzer Component 13 and also to the Movement component 17.

The Analyser Component 19: With reference to FIG. 23, the Analyser Component collects the information from the pulse component 15, Oxygen Saturation Component 16. Movement Component 17 and Respiration Component 18. During periods of detected motion or other signal artifact the analyser makes a decision to hold the most appropriate recent values of these signals until the artifact event passes or until predetermined interval has passed at which point an alarm signal sent to the device output 20. Further the analyzer checks the incoming signals for anomalous behaviour including, but not limited to: low and or high pulse rates, pulse irregularities, low and high breathing rates, breathing irregularities, low and high oxygen saturation rates, movement irregularities including excessive movement and absence of movement. Detected anomalous behaviour or combination of behaviours will trigger an alarm signal sent to the device output 20.

4.2 Physical Attachment of Probes and Transmission of PPG Signals

Referring to FIG. 23, the acquisition of the signal 10 takes place at a suitable site on the patient's body. This signal is then sent to component 11 where the signals are digitized then to component 12 where their natural logarithm is computed prior to the wavelet analysis at 13. The patient signal may be taken using a standard probe configuration. For example a finger or toe probe, foot probe, forehead probe, ear probe and so on. Further the probe may function in either transmittance or reflectance mode.

Figure 27:
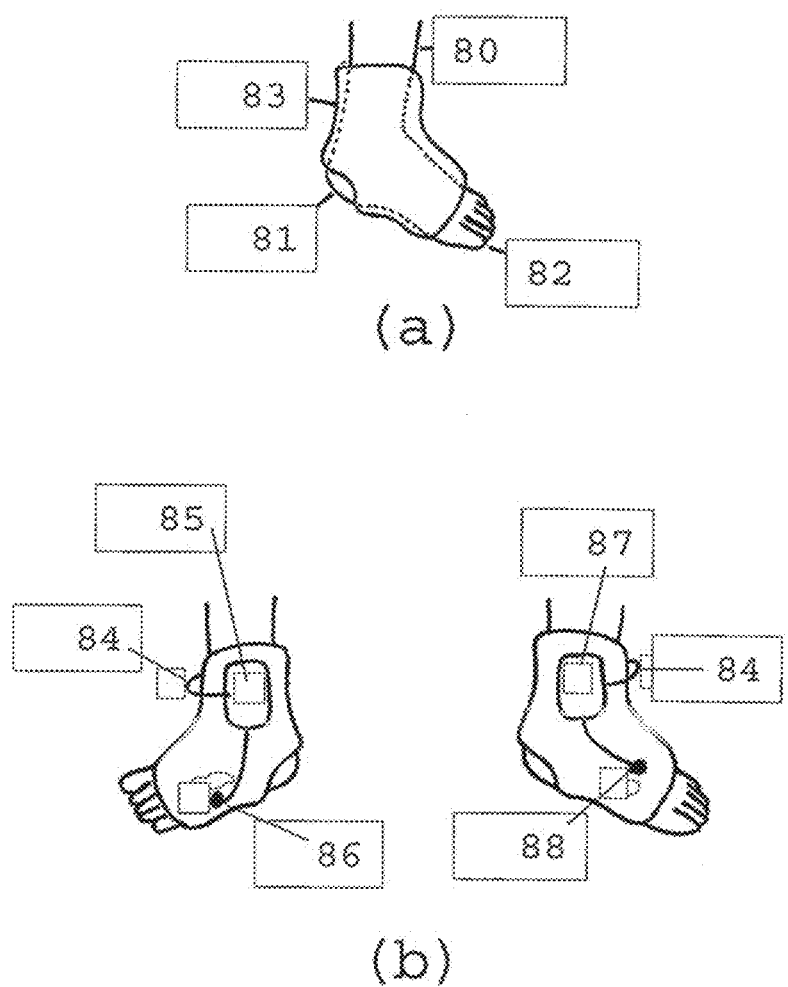
Figure 28:
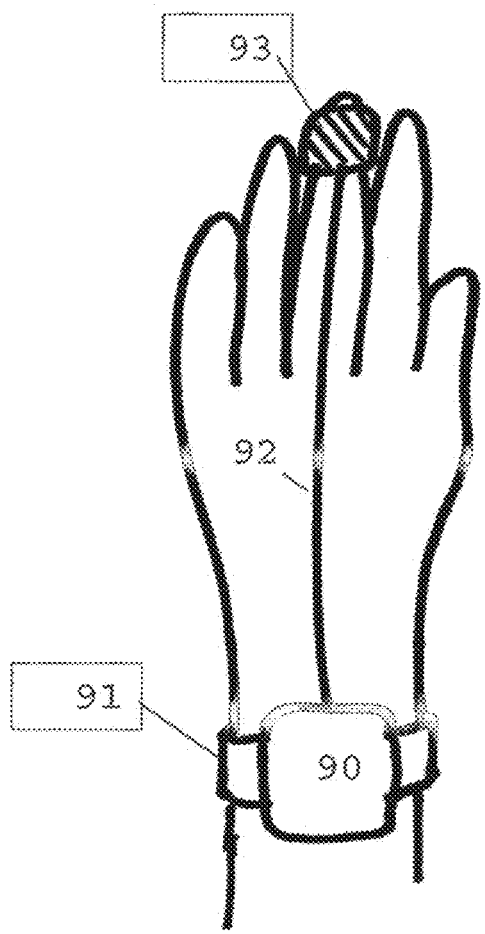

In one preferred embodiment for use with neonates a foot/ankle mounted device such as a cuff is employed as depicted schematically in FIG. 27. The cuff is used to house the probe electronics, radio frequency transmitter modules and battery. FIG. 27(a) shows the patients lower leg 80 and foot with the preferred embodiment of the cuff 83 attached to the foot. The patients heel 81 and toes 82 protrude from the cuff. FIG. 27(b) shows two views, one from each side of the foot showing the cuff with compartments for housing the electronic equipment required for signal acquisition and transmission. The PPG signals may be taken directly through the foot using Light Emitting Diodes (LEDs) 86 and photodetector 88 located as shown or, in an alternative embodiment, they may be taken at the toe using a short length of cable attaching the pulse oximeter probe to the electronics contained in the cuff. In a further alternative embodiment reflectance mode photoplethysmography may be employed. In a further alternative embodiment more suitable for adult monitoring the electronic equipment is packaged within a soft housing which is wrapped and secured around the wrist as shown in FIG. 28. The electronic components for receiving processing and transmitting the PPGs are housed in a unit 90 secured by a band 91 to the patients wrist. The PPG signals are acquired at a site local to the wrist band. For example from a finger 93 via a lead 92 from the wrist unit 90, or at the site of the wrist band and housing using, for example, reflectance mode photoplethysmography. In yet another alternative embodiment, the signal from the pulse oximeter probe would be sent to the monitor device using a physical lead instead of the wireless method described here.

Light transmitters other than LEDs may be used in the device without departing from the scope of the invention.

In an alternative embodiment, the digitised signal from 11 may input directly to the wavelet transform component 13 without taking the natural logarithm. In an alternative embodiment, more than two wavelengths or combination of more than two wavelengths of light may be employed in the Oximetry method.

4.3 Use of the Device

4.3.1 General Use

The device may be need, for general patient monitoring in the hospital, home, ambulatory or other environment. For example in a preferred embodiment for a device for use within a hospital setting it may be used to continually or intermittently monitor patient respiration together with oxygen saturation and pulse rate.

4.3.2 Embodiment as an Apnea Monitor

In another preferred embodiment of the device it would be used as an apnea monitor. Apnea is the cessation of breathing usually occurring during sleep. There is increasing awareness of this sleep disorder as the cause of a number of serious medical conditions in adults and infants. Separate areas of use are envisaged for the device as an apnea monitor. Examples of this use include, but are not limited to: (1) adult monitoring, where it can be used as a home screening diagnostic tool for potential apnea patients and (2) infant monitoring, where it can be used as either an in hospital or home monitoring tool to alert the child's carer to this potentially fatal respiration irregularity.

Apnea monitors monitor heart and respiratory signals to detect apnea episodes—usually defined as cessation of breathing for >20 seconds. Apnea is associated with slowing of the pulse (bradycardia) or bluish discoloration of the skin due to lack of oxygenated haemoglobin (cyanosis). Long term effects of apnea in adults are quite serious and have been reported to include: heavy snoring, weariness and obsessive drive to fall asleep, reduced physical and mental fitness, strokes, nervousness, fall in concentration and headaches, psychic symptoms up to depressions, sexual dysfunctions, impotence, dizziness and nightly perspiration. In babies apnea may lead to death if suitable resuscitation measures are not taken.

As it measures respiration and movement directly from the pulse oximeter signal (in addition to oxygen saturation and pulse), the device can be fitted remote from the head; e.g. the foot or arm of the patient. This has the advantage over current devices which comprise of probes located on the patients head and face to measure breathing at the patients nose and/or mouth. As such they are uncomfortable for adult patients and are quite impractical for fitting to babies for the obvious reason of causing a potential choking hazard. The preferred embodiment of our invention allows the PPG signal collected at the patient to be sent via a wireless link to a remotely located device.

In summary, embodied as an apnea monitor, the device provides a method for the acquisition analysis and interpretation of pulse oximeter signals to provide clinically useful information on patient pulse rate, oxygen saturation, respiration and movement. From a combination of some or all of this information clinical decisions can be made with regard to the patient's health. The patient respiration information is used to monitor the patient in order to compute a respiration rate and to detect breathing abnormalities, for example: apnea events, cessation in breathing, sharp intakes of breaths, coughing, excessively fast breathing, excessively slow breathing, etc. Information derived from one or more of the respiration, movement, oxygen saturation and pulse measurements may be used to trigger an alarm to call for medical help or to initiate an automated process for the administration of a therapeutic intervention. A method may be employed for the archiving of the derived signals during the analysis period of the patient which may be at a later date for analysis by the clinician.

The device may be used to monitor the patient both during sleep and when awake.

The device may be used to detect the onset of sudden infant death syndrome SIDS by detecting and analysing abnormalities in the measurement of one or more of the following; oxygen saturation, respiration, movement and pulse.

4.3.3 Alarm

As described above, it is envisaged that the gathered information is used to trigger an alarm at the bedside and/or at a remote nursing station. This alarm would be graded according to a classification of patient information. For example a reduction in oxygen saturation below a predefined threshold with associated loss or irregularity of patient movement, irregularity of pulse rate and loss or irregularity of patient respiration could trigger the highest level of alarm, whereas a reduction of oxygen saturation be low a predefined threshold with a normal level of patient movement and/or a regular respiration pattern, could trigger a lower level of alarm.

5. BRIEF DESCRIPTION OF DRAWINGS

FIG. 1(a): A wavelet transform surface showing the pulse band (located between the dashed lines). (High to Low energy is graded from white to black in the grey scale plot.)

FIG. 1(b): Three-dimensional view of the wavelet transform surface of FIG. 1(a) showing the maxima of the pulse band with respect to frequency (the ridge) superimposed as a black path across the band maxima (High to bow energy is graded from white to black in the grey scale plot.)

FIG. 2: 3-D Schematic of a wavelet transform surface containing two bands. The locus of the local maxima, on the bands (the 'ridges') are shown by dashed lines.

FIG. 3. Schematics of the RAP (top left) and RFP (top right) signals derived from ridge A in FIG. 1 together with their corresponding wavelet transforms shown below each (in 2D).

FIG. 4(a): The SWFD method as applied to a pulse oximeter signal—Scalogram of Original Signal. (High to Low energy is graded from white to black in the grey scale plot.)

FIG. 4(b): The SWFD method as applied to a pulse oximeter signal—3-D view of scalogram in (a) with the path of the pulse band ridge superimposed. (High to Low energy is graded from white to black in the grey scale plot.)

FIG. 4(c): The SWFD method as applied to a pulse oximeter signal—RAP signal (Top: full signal. Lower; blow up of selected region)

FIG. 4(d): The SWFD method as applied to a pulse oximeter signal—RFP signal (Top: full signal. Lower; blow up of selected region)

FIG. 5(a): The SWFD method as applied to a pulse oximeter signal—RAP scalogram. (High to Low energy is graded from white to black in the grey scale plot.)

FIG. 5(b): The SWFD method as applied to a pulse oximeter signal—RFP scalogram. (High to Low energy is graded from white to black in the grey scale plot.)

FIG. 5(c): The SWFD method as applied to a pulse oximeter signal—3-D view of RAP scalogram with breathing band ridge shown. (High to Low energy is graded from white to black in the grey scale plot.)

FIG. 5(d): The SWFD method as applied to a pulse oximeter signal—3-D view of RFP scalogram with ridge shown, (High to Low energy is graded from white to black in the grey scale plot.)

FIG. 6(a): PPG Signal

FIG. 6(b): Pulse band and ridge corresponding to signal (a). (High to Low energy is graded from white to black in the grey scale plot.)

FIG. 6(c): RAP signal derived from ridge in (b) with breathing switch (square waveform) superimposed.

FIG. 6(d): RFP signal derived from ridge in (b)

FIG. 7(a): Wavelet Transform of RAP signal. (High to Low energy is graded from white to black in the grey scale plot.)

FIG. 7(b): Extracted ridges from wavelet transform in (a). (High to Low energy is graded from white to black in the grey scale plot.)

FIG. 7(c): Wavelet Transform of RFP signal. (High to Low energy is graded from white to black in the grey scale plot.)

FIG. 7(d): Extracted ridges from wavelet transform in (c). (High to Low energy is graded from white to black in the grey scale plot.)

FIG. 8(a): Breathing ridges extracted from the original wavelet transform

FIG. 8(b): Breathing ridges extracted from the secondary wavelet transform of the RAP signal FIG. 8(c): Breathing ridges extracted from the secondary wavelet transform of the RFP signal FIG. 8(d): Selected respiration path (SRP), FIG. 9: Transform Phase along the SRP FIG. 10: Filling in missing segments of the SRP FIG. 11: Wavelet Representations of the Red PPG (top) and Infrared PPG (bottom)

Figure 12:
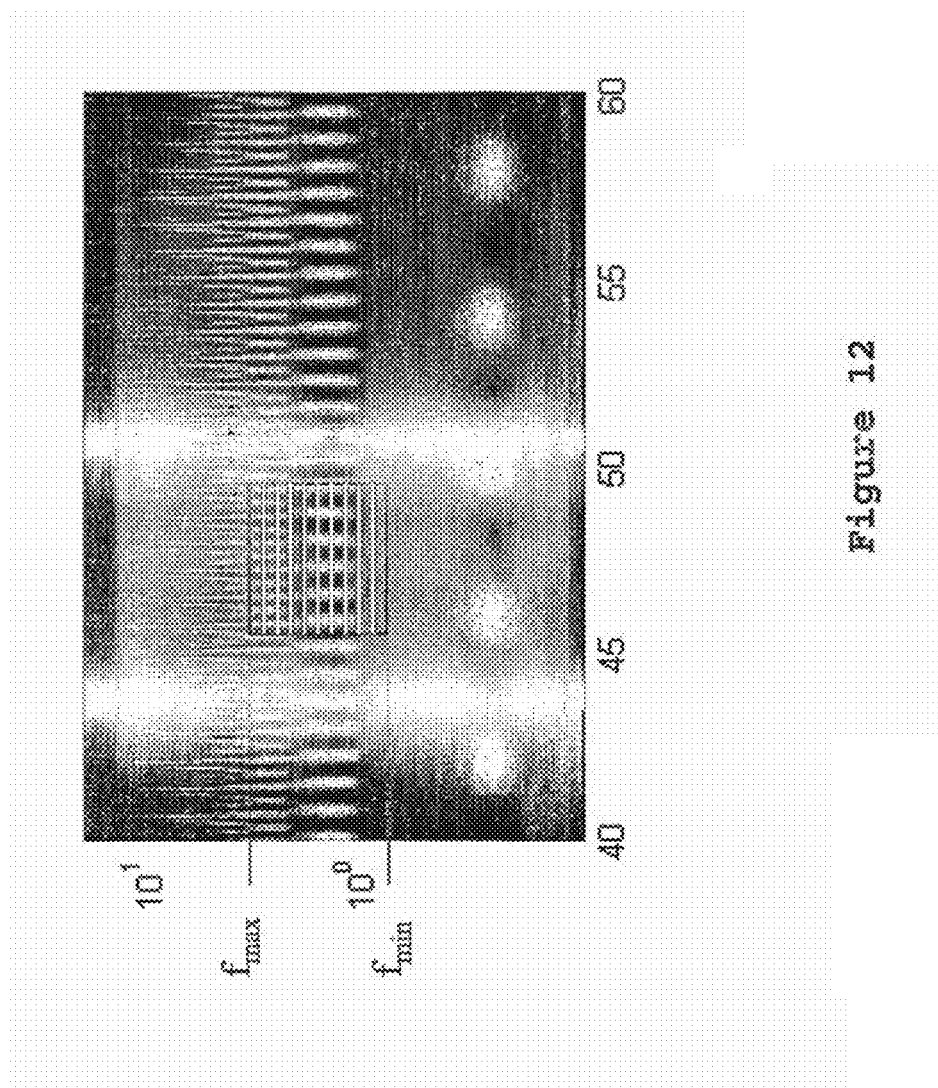

FIG. 12: Schematic of the Sliding Window used to Obtain the Wavelet Components for the 3-D Lissajous FIG. 13(a): Wavelet-based 3-Lissajous: 3-D View.

FIG. 13(b): Wavelet-based 3-D Lissajous: End on View of (a).

FIG. 13(c): Wavelet-based 3-D Lissajous: End on View of Selected Component.

FIG. 14: Standard Deviation of Lissajous Components in FIG. 3. Top plot: SD of principle component; Middle plot: SD of minor component; Lower plot: Ratio of SD components. All three plots plotted against frequency in Hz.

FIG. 15: Computed Oxygen Saturation curves. Dotted line: Signal Amplitude Method; Dashed Line traditional Signal Lissajous Method; Solid Line: Wavelet-based 3-D Lissajous Method.

FIG. 16: The red and infrared wavelet modulus surfaces corresponding to a 45 second segment of PPG signals. (High to Low energy is graded from white to black in the grey scale plot.)

FIG. 17: The wavelet ratio surface derived from the division of the red by the infrared wavelet representations shown in FIG. 16.

FIG. 18: An end view of the wavelet ratio surface shown in FIG. 17.

FIG. 19: Computed Oxygen Saturation curves. Dotted lines: Oxygen Saturation from Traditional Signal Amplitude Method; Dashed Line: Oxygen Saturation from Traditional Signal Lissajous Method; Solid Line: Oxygen Saturation from Traditional Wavelet-Ratio Surface Method FIG. 20(a): Wavelet transform plot of a PPG signal taken from a young baby showing a corresponding to patient movement. Low to high energy is depicted from black to white in the greyscale plot.

FIG. 20(b): Three-dimensional view of (a). Low to high energy is depicted from black to white in the greyscale plot.

FIG. 21(a): Transform plot of FIG. 20(a) with modulus maxima superimposed. Low to high energy is depicted from black to white in the grayscale plot.

FIG. 21(b): Three-dimensional view of FIG. 21(a). Low to high energy is depicted from black to white in the greyscale plot.

FIG. 22(a): End view of modulus maxima lines in FIG. 21(b).

FIG. 22(b): Amplitude threshold method of identifying modulus maxima associated with movement artefact FIG. 22(c): Pulse ridge-based method of identifying modulus maxima associated with movement artefact FIG. 22(d): Respiration ridge-based method of identifying modulus maxima associated with movement artefact FIG. 23: Block diagram of device configuration FIG. 24: Block diagram of subcomponents of oxygen saturation component (16) shown in FIG. 23

FIG. 25: Block diagram of subcomponents of respiration component (18) shown in FIG. 23

FIG. 26: Block diagram of subcomponents of movement component (17) shown in FIG. 23

FIG. 27(a): Schematic of foot cuff mounting: soft housing surrounding foot used to hold monitoring apparatus.
80 patient leg; 81 patient heel; 82 patient toes; 83 soft housing surrounding foot FIG. 27(b): View from both sides of the envisaged device: preferred embodiment for neonatal monitor. 84 connection cabling; 85 RF components attached to housing; 86 LEDs; 87 pulse oximeter components attached to housing; 88 photodetector. (Note LEDs and photodetector may also be located on toe using short cable length from cuff.)

FIG. 28: Schematic of wrist cuff mounting; 90 electronic component housing; 91 wrist band; 92 connector cable; 93 finger probe

6. GENERAL

The invention has been described and shown with specific reference to specific embodiments. However it will be understood by those skilled in the art that changes to the form and details of the disclosed embodiments may be made without departing from the spirit and scope of the invention. For example signal transforms other than the wavelet transform may be used. Other variations may include using a multiplexed arrangement which alternates measurements for pulse, oxygen saturation, respiration and movement artefact using variations of the acquisition equipment and transmission electronics. These variations may include but are not limited to the use of more than two wavelengths of light and variable power and/or variable duty cycle to the light transmitters.

7. REFERENCE

Addison P. S., 'The Illustrated Wavelet Transform Handbook', Institute of Physics Publishing, 2002, Bristol, UK.

The invention claimed is:

1. A method for determining an artifact pertaining to physiological movement, comprising:
   obtaining a photoplethysmographic (PPG) biosignal from a subject at least in part using a signal acquisition unit;
   decomposing, using a signal processor, the PPG biosignal at least in part using a wavelet transform analysis to obtain transform data, the transform data comprising a time axis, a scale axis, and an amplitude axis;
   identifying, using the signal processor, a plurality of amplitude maxima points in the transform data in the direction of the time axis;
   setting, using the signal processor, an amplitude threshold;
   determining, using the signal processor, the artifact pertaining to physiological movement based at least in part on the plurality of amplitude maxima points and the amplitude threshold;
   determining, using the signal processor, a physiological parameter of the subject based at least in part on the PPG biosignal, the physiological parameter comprising at least on of: respiration rate, pulse rate, and oxygen saturation; and
   determining, using the signal processor, a confidence measurement pertaining to the physiological parameter based at least in part on determining the artifact.

2. The method of claim 1, wherein the signal acquisition unit comprises a photodetector.

3. The method of claim 1, wherein the transform data comprises data for a set of scales.

4. The method of claim 3, wherein the set of scales includes one or more scales corresponding to a pulse ridge and the amplitude threshold is based at least in part on a mean value of the pulse ridge.

5. The method of claim 3, wherein the set of scales includes one or more scales corresponding to a respiration ridge and the amplitude threshold is based at least in part on a mean value of the respiration ridge.

6. The method of claim 1, further comprising:
   determining, using the signal processor, a region containing the artifact in the time-scale plane of the transform data; and
   defining, using the signal processor, in the region, a cone of influence of the artifact based at least in part on the widths of the wavelet function used in the wavelet transform analysis.

7. The method of claim 6, wherein the widths of the wavelet function are based at least in part on a standard deviation of temporal spread.

8. The method of claim 1, further comprising holding, using the signal processor, measurements pertaining to a physiological parameter at a previous value based at least in part on the artifact.

9. The method of claim 1, further comprising:
   identifying, using the signal processor, the plurality of amplitude maxima points in the transform data in the direction of the time axis for at least two scales;
   setting, using the signal processor, one or more amplitude thresholds for the at least two scales; and
   determining, using the signal processor, the artifact pertaining to physiological movement based at least in part on the plurality of amplitude maxima points for the at least two scales and the one or more amplitude thresholds.

10. A monitoring system for determining an artifact pertaining to physiological movements, the system comprising:
    a signal acquisition unit attachable to a subject to obtain a photoplethysmographic (PPG) biosignal; and
    a signal processor configured to:
      decompose the PPG biosignal at least in part using a wavelet transform analysis to obtain transform data, the transform data comprising a time axis, a scale axis, and an amplitude axis;
      identify a plurality of amplitude maxima points in the transform data in the direction of the time axis;
      set an amplitude threshold;
      determine the artifact pertaining to physiological movement based at least in part on the plurality of amplitude maxima points and the amplitude threshold;
      determine a physiological parameter of the subject based at least in part on the PPG biosignal, the physiological parameter comprising at least on of: respiration rate, pulse rate, and oxygen saturation; and
      determine a confidence measurement pertaining to the physiological parameter based at least in part on determining the artifact.

11. The system of claim 10, wherein the signal acquisition unit comprises a photodetector.

12. The system of claim 10, wherein the transform data comprises data for a set of scales.

13. The system of claim 12, wherein the set of scales includes one or more scales corresponding to a pulse ridge and the amplitude threshold is based at least in part on a mean value of the pulse ridge.

14. The system of claim 12, wherein the set of scales includes one or more scales corresponding to a respiration ridge and the amplitude threshold is based at least in part on a mean value of the respiration ridge.

15. The system of claim 10, wherein the signal processor is further configured to:
   determine a region containing the artifact in the time-scale plane of the transform data; and
   define, in the region, a cone of influence of the artifact based at least in part on the widths of the wavelet function used in the wavelet transform analysis.

16. The system of claim 15, wherein the widths of the wavelet function are based at least in part on a standard deviation of temporal spread.

17. The system of claim 10, wherein the signal processor is further configured to hold measurements pertaining to a physiological parameter at a previous value based at least in part on the artifact.

18. The system of claim 10, wherein the signal processor is further configured to:
   identify the plurality of amplitude maxima points in the transform data in the direction of the time axis for at least two scales;
   set one or more amplitude thresholds for the at least two scales; and
   determine the artifact pertaining to physiological movement based at least in part on the plurality of amplitude maxima points for the at least two scales and the one or more amplitude thresholds.

* * * * *